United States Patent
Volles et al.

(10) Patent No.: US 11,697,815 B2
(45) Date of Patent: Jul. 11, 2023

(54) REGULATION OF GENE EXPRESSION THROUGH APTAMER-MODULATED POLYADENYLATION

(71) Applicant: MeiraGTx UK II Limited, London (GB)

(72) Inventors: Michael J. Volles, Cambridge, MA (US); Olivier F. Danos, Boston, MA (US); Xuecui Guo, Cold Spring Harbor, NY (US)

(73) Assignee: MEIRAGTX UK II LIMITED, London (GB)

( * ) Notice: Subject to any disclaimer, the term of this patent is extended or adjusted under 35 U.S.C. 154(b) by 375 days.

(21) Appl. No.: 16/074,657

(22) PCT Filed: Feb. 2, 2017

(86) PCT No.: PCT/US2017/016279
§ 371 (c)(1),
(2) Date: Aug. 1, 2018

(87) PCT Pub. No.: WO2017/136591
PCT Pub. Date: Aug. 10, 2017

(65) Prior Publication Data
US 2020/0017858 A1    Jan. 16, 2020

Related U.S. Application Data

(60) Provisional application No. 62/290,200, filed on Feb. 2, 2016.

(51) Int. Cl.
| | | |
|---|---|---|
| *C12N 15/11* | (2006.01) | |
| *C12N 15/115* | (2010.01) | |
| *A61K 48/00* | (2006.01) | |
| *C12N 15/113* | (2010.01) | |
| *C12N 15/86* | (2006.01) | |

(52) U.S. Cl.
CPC ........ *C12N 15/115* (2013.01); *A61K 48/0008* (2013.01); *A61K 48/0066* (2013.01); *C12N 15/113* (2013.01); *C12N 15/86* (2013.01); *C12N 2310/16* (2013.01); *C12N 2830/42* (2013.01)

(58) Field of Classification Search
CPC .......................... C12N 15/115; A61K 48/0066
See application file for complete search history.

(56) References Cited

U.S. PATENT DOCUMENTS

| | | |
|---|---|---|
| 2003/0082149 A1 | 5/2003 | Rowe et al. |
| 2009/0170793 A1 | 7/2009 | Gaur |
| 2010/0173407 A1 | 7/2010 | Wypijewski et al. |
| 2011/0245326 A1 | 10/2011 | Belmont et al. |
| 2012/0107331 A1 | 5/2012 | Strobel et al. |
| 2015/0099796 A1 | 4/2015 | Gunderson et al. |

FOREIGN PATENT DOCUMENTS

| | | |
|---|---|---|
| WO | 2008/121963 A2 | 10/2008 |
| WO | 2010/132665 A1 | 11/2010 |
| WO | 2014/008474 A1 | 1/2014 |
| WO | 2016/126747 A1 | 8/2016 |
| WO | 2018/025085 A2 | 2/2018 |

OTHER PUBLICATIONS

Fortes et al, Inhibiting expression of specific genes in mammalian cells with 5' end-mutated U1 small nuclear RNAs targeted to terminal exons of pre-mRNA, 2003, PNAS, vol. 100, No. 14, pp. 8264-8269. (Year: 2003).*
Malca, H. et al., "The U1 snRNP Base Pairs with the 5' Splice Site Withing a Penta-snRNP Complex"; Mol. Cell. Biol. (2003); vol. 23:10; pp. 3442-3455.
Kim, D. et al., "An Artificial Ribswitch for Controlling pre-mRNA Splicing"; RNA (2005); vol. 11; pp. 1667-1677.
Berens, C. et al., "RNA Aptamers as Genetic Control Devices: The Potential of Riboswitches as Synthetic Elements for Regulating Gene Expression"; Biotechnology Journal (2015); vol. 10:2; pp. 246-257.
Groher, F. et al., "Syntehtic Riboswitches—A Tool Comes of Age"; Biochimica et Biophysica ACTA Gene (2014); vol. 10; pp. 964-973.
Whittmann, A. et al., "Engineered Riboswitches: Expanding Researchers Toolbox with Syntehtic RNA Regulators"; FEBS Letters (2012); vol. 586.15; pp. 2076-2083.
Weigand, J. et al., "Tetracycline Aptamer-Controlled Regulation of Pre-mRNA Splicing in Yeast"; Nucleic Acids Research (2007); vol. 35:12; pp. 4179-4185.
Fortes, P. et al., "Inhibiting Expression of Specific Genes in Mammalian Cells with 5' end-mutated U1 Small Nuclear RNAs Targeted to Terminal Exons of Pre-mRNA"; PNAS US (2003); vol. 100:14; pp. 8264-8269.
Roca, X. et al., "Pick One, but be Quick: 5' Splice Sites and the Problems of too many choices"; Genes & Development (2013); vol. 27:2; pp. 129-144.
Denisov, D. A. et al., "Hierarchical Structure of Donor Splice Site Sequence Multitude"; Gene (2003); vol. 320, pp. 89-96.
Fortes, P. et al., "Inhibiting Expression of Specific Genes in Mammalian Cells with 5' end-mutated U1 Small Nuclear RNAs Targeted to Terminal Exons of Pre-mRNA"; PNAS US (2003); vol. 100:14; pp. 8264-8269. Supporting Text accessed at https://www.pnas.org/doi/10.1073/pnas.1332669100#supplementary-materials <https://www.pnas.org/doi/10.1073/pnas.1332669100>.

\* cited by examiner

*Primary Examiner* — Ekaterina Poliakova-Georgantas
(74) *Attorney, Agent, or Firm* — Fox Rothschild LLP

(57) ABSTRACT

The invention provides polynucleotide constructs for the regulation of gene expression by aptamer-based modulation of U1 small nuclear ribonucleoprotein (snRNP)-mediated suppression of polyadenylation and methods of using the constructs to regulate gene expression in response to the presence or absence of a ligand that binds the aptamer. The polynucleotide construct contains a U1 binding site in the context of a riboswitch comprising an effector region and an aptamer such that when the aptamer binds a ligand, target gene expression occurs.

30 Claims, 12 Drawing Sheets

Specification includes a Sequence Listing.

| Construct | Sequence | Length (nt) |
|---|---|---|
| U1-87 | 5' CA<u>GG</u><u>T</u>AA<u>G</u>TA 3' | 10 |
| 87-9 | 5' CAGGTAAGT 3' | 9 |
| 87-8 | 5' CAGGTAAG 3' | 8 |
| 87-7 | 5' CAGGTAA 3' | 7 |
| 87-6 | 5' CAGGTA 3' | 6 |
| 87-5 | 5' CAGGT 3' | 5 |

Progressive deletion ↓ single U1 site 87-9 in stem loop    single U1 site 87-9 with broken stem

REGULATION OF GENE EXPRESSION THROUGH APTAMER-MODULATED POLYADENYLATION

FIELD OF THE INVENTION

The invention provides polynucleotide constructs for the regulation of gene expression by aptamer-based modulation of U1 snRNP-mediated suppression of polyadenylation and methods of using the constructs to regulate gene expression in response to the presence or absence of a ligand that binds the aptamer. The polynucleotide construct contains a U1 binding site in the context of a riboswitch comprising an effector region and an aptamer such that when the aptamer binds a ligand, target gene expression occurs.

Sequence Listing

A Sequence Listing is provided herewith as a text file, called, "162027-46501_Sequence-Listing_ST25", created on Apr. 6, 2021 and having a size of 26 kb. The contents of the text file are incorporated herein by reference in their entirety.

BACKGROUND OF THE INVENTION

Messenger RNAs (mRNAs) in eukaryotic cells are produced from pre-mRNA transcripts by extensive post-transcriptional processing, including 5' end capping, removal of introns by splicing, and 3' end cleavage and polyadenylation. Splicing is performed by a spliceosome, a large RNA-protein complex comprised predominantly of small nuclear ribonucleoproteins (snRNPs). The predominant (U2-type) spliceosome contains the U1, U2, U4, U6 and U5 snRNPs, whereas a much less abundant U12-type spliceosome is comprised of U11, U12, U4atac, U6atac and U5 snRNPs.

The 3' end of almost all eukaryotic mRNAs comprises a poly(A) tail—a homopolymer of 20 to 250 adenosine residues. The poly(A) tail is added to pre-mRNA in the nucleus by cleavage and polyadenylation, a process catalyzed by a large complex of proteins. In vertebrates, addition of a poly(A) tail depends on two cis-acting RNA elements, the highly conserved AAUAAA polyadenylation sequence found upstream of the polyadenylation site and a poorly conserved GU-rich element found downstream. Addition of a poly(A) tail to mRNA protects it from degradation, among other functions.

The U1 snRNP has been shown to have splicing-independent function in pre-mRNA processing by suppressing 3' end processing of pre-mRNA, inhibiting aberrant intronic polyadenylation signal, and ensure promoter directionality. For example, Fortes et al. (*PNAS*, 100:8264-69, incorporated herein by reference), placed one to three U1 binding sites in the 3' UTR leading to reduced reporter gene expression.

SUMMARY OF THE INVENTION

In one aspect, the present invention provides a polynucleotide cassette for the regulation of the expression of a target gene comprising a riboswitch wherein the riboswitch comprises an effector region and an aptamer, wherein the effector region comprises a U1 snRNP binding site and sequence complementary to the U1 snRNP binding site. In one embodiment, the aptamer binds a small molecule ligand.

In one embodiment, the effector sequence comprises, in addition to the U1 snRNP binding site and sequence complementary to the U1 snRNP binding, additional sequence that is capable of forming a stem when the aptamer binds ligand. In one embodiment, the effector region comprises a stem-forming sequence that is 9 to 11 base pairs. In one embodiment, the effector region comprises a stem-forming sequence with one or more mismatched bases in the stem.

In one embodiment, the U1 snRNP binding site is 8 to 10 nucleotides. In one embodiment, the U1 snRNP binding site comprises the sequence CAGGTAAG. In one embodiment, the U1 snRNP binding site is selected from the group consisting of CAGGTAAGTA, CAGGTAAGT, and CAGGTAAG.

In one embodiment, the polynucleotide cassette comprises two or more riboswitches, wherein each riboswitch comprises an effector region and an aptamer, wherein the effector region comprises a U1 snRNP binding site and sequence complementary to the U1 snRNP binding site. In one embodiment, the two or more riboswitches each comprise an aptamer that binds the same ligand. In one embodiment, the two or more riboswitches comprise different aptamers that bind different ligands.

In another aspect, the present invention provides a method of modulating the expression of a target gene comprising:
(a) inserting one or more of the polynucleotide cassettes described above into the 3' UTR of a target gene,
(b) introducing the target gene comprising the polynucleotide cassette into a cell, and
(c) exposing the cell to a ligand that specifically binds the aptamer in an amount effective to increase expression of the target gene.

In one embodiment, the ligand is a small molecule.

In one embodiment, the polynucleotide cassette is inserted about 87 and/or about 140 nucleotides 5' of the polyadenylation signal. In one embodiment, the polynucleotide cassette is inserted at one or more of about 74, about 110, or about 149 nucleotides 5' of the polyadenylation signal.

In one embodiment, two or more of the polynucleotide cassettes are inserted into the 3' UTR of the target gene. In one embodiment, the two or more polynucleotide cassettes comprise different aptamers that specifically bind to different small molecule ligands. In one embodiment, the two or more polynucleotide cassettes comprise the same aptamer. In one embodiment, the two or more polynucleotide cassettes are inserted at different locations of the 3' UTR of the target gene.

In another aspect, the present invention provides a target gene comprising a polynucleotide cassette described above incorporated in a vector for the expression of the target gene. In one embodiment, the vector is a viral vector. In one embodiment, the viral vector is selected from the group consisting of adenoviral vector, adeno-associated virus vector, and lentiviral vector.

In another aspect, the present invention provides a vector comprising a target gene that contains a polynucleotide cassette described herein. In one embodiment, the vector is a viral vector. In one embodiment, the viral vector is selected from the group consisting of adenoviral vector, adeno-associated virus vector, and lentiviral vector.

BRIEF DESCRIPTION OF THE FIGURES

FIG. 1*a*. Schematics for the insertion of U1 binding sequence in 3' UTR at different position in pRL-SV40 vector. The wild type (SEQ ID NO: 1) and mutant (SEQ ID NO: 2) U1 consensus binding sequences are listed.

FIG. 1b. Results of Renilla luciferase assay. HEK 293 cells were transfected with the indicated constructs containing at various positions in the 3' UTR either the consensus U1 binding sequence or the mutant sequence. The results were expressed as mean±SD (n=3), and the reduction fold was calculated as ratio of luciferase activity from mutant construct to luciferase activity from wild type construct. Consensus sequence constructs include U1-87 wt (SEQ ID NO: 3), U1-140 wt (SEQ ID NO: 5), 2×U1-140 wt (SEQ ID NO: 7), and 3×U1-140 wt (SEQ ID NO: 9). Mutant sequence constructs include U1-87 mut (SEQ ID NO: 4), U1-140 mut (SEQ ID NO: 6), 2×U1-140 mut (SEQ ID NO: 8), and 3×U1-140 mut (SEQ ID NO: 10).

FIG. 2a. The full length (U1-87) and the truncated sequences (87-9, 87-8, 87-7, 87-6, and 87-5) of U1 binding sites inserted at –87 position in 3' UTR. Sequences in the constructs include: U1-87 (SEQ ID NO:3); 87-9 (SEQ ID NO: 11), 87-8 (SEQ ID NO: 12); 87-7 (SEQ ID NO: 13); 87-6 (SEQ ID NO: 14); and 87-5 (SEQ ID NO: 15).

FIG. 2b. HEK 293 cells were transfected with the indicated constructs containing full length or truncated U1 binding sequences inserted at −87 and luciferase activity was determined. Indicated construct sequences include: U1-87 wt (SEQ ID NO:3); 87-9 (SEQ ID NO: 11), 87-8 (SEQ ID NO: 12); 87-7 (SEQ ID NO: 13); 87-6 (SEQ ID NO: 14); 87-5 (SEQ ID NO: 15); and U1-87 mut (SEQ ID NO:4).

FIG. 3a. The sequence of the stem-loop structure that embedded the U1 binding site in the stem (SEQ ID NO: 16). Mutations were made to generate a broken stem (shown on right SEQ ID NO: 17).

FIG. 3b. Results of luciferase activity assay indicate that the stem-loop structure sequestering the U1 binding site completely abolished the suppressive effect of U1 interference on gene expression. Constructs indicated include: U1 87-9 (SEQ ID NO: 11); U1 87-9 stem loop (SEQ ID NO: 16); and U1 87-9 stem loop broken (SEQ ID NO: 17).

FIG. 4a. The schematics showing the aptamer-modulated U1 interference in 3' UTR and gene expression. In the absence of aptamer ligand (top panel), a U1 site inserted in the 3' UTR is available for U1 snRNP binding and U1-mediated polyadenylation interference, thus suppressing target gene expression. In the presence of aptamer ligand (lower panel), aptamer/ligand binding leads to the formation of stem which sequesters the U1 binding site from U1 snRNP binding. U1-mediated polyadenylation interference is abolished, resulting in target gene expression.

FIG. 4b. The sequence of the effector region stem that sequesters the U1 binding site and connects the theophylline aptamer, generated by serial truncation of the hairpin stem and lower stem of theophylline aptamer. Shown are the stem sequences for constructs U1 theo_1 (SEQ ID NO: 18), U1 theo_8 (SEQ ID NO: 25), and U1 theo_9 (SEQ ID NO: 26). Theophylline is shown as.

FIG. 4c. HEK 293 cells were transfected with the indicated constructs, and treated with or without 3 mM theophylline. The induction fold was calculated as the ratio of the value of luciferase activity obtained from theophylline treated cells to the luciferase activity obtained from untreated cells. Constructs indicated include: U1 87-9 (SEQ ID NO: 11); U1 87-9 SL (SEQ ID NO: 16); U1 87-9 SL... (broken) (SEQ ID NO: 17); U1 87 mut (SEQ ID NO: 4); U1 theo_1 (SEQ ID NO: 18), U1 theo_2 (SEQ ID NO: 19), U1 theo_3 (SEQ ID NO: 20), U1 theo_4 (SEQ ID NO: 21), U1 theo_5 (SEQ ID NO: 22), U1 theo_6 (SEQ ID NO: 23), U1 theo_7 (SEQ ID NO: 24), U1 theo_8 (SEQ ID NO: 25), and U1 theo_9 (SEQ ID NO: 26).

FIG. 5a. The stem sequences of U1 theo_8 (SEQ ID NO: 25) and U1_theo_9 (SEQ ID NO: 26), with the sequential mutations listed beside corresponding nucleotides. The sequential mutations create a mismatch in the effector region stem.

FIG. 5b. A total of 9 constructs were generated through sequential mutation of U1_theo_8 and were each transfected into HEK 293 cells. Transfected cells were treated with or without 3 mM theophylline and luciferase activity measured. The results were expressed as mean±SD, and the induction fold was indicated for construct U1_theo_8 to U1_8_5. Constructs indicated include: U1 87-9 (SEQ ID NO: 11); U1 87-9 SL (SEQ ID NO: 16); U1 87-9 SL... (broken) (SEQ ID NO: 17); U1 87 mut (SEQ ID NO: 4); U1 theo_8 (SEQ ID NO: 25), U1 theo_8_1 (SEQ ID NO: 27), U1 theo_8_2 (SEQ ID NO: 28), U1 theo_8_3 (SEQ ID NO: 29), U1 theo_8_4 (SEQ ID NO: 30), U1 theo_8_5 (SEQ ID NO: 31), U1 theo_8_6 (SEQ ID NO: 32), U1 theo_8_7 (SEQ ID NO: 33), U1 theo_8_8 (SEQ ID NO: 34), and U1 theo_8_9 (SEQ ID NO: 35).

FIG. 5c. A total of 8 constructs were generated through sequential mutation of U1_theo_9 and were each transfected into HEK 293 cells. Transfected cells were treated with or without 3 mM theophylline and luciferase activity measured. The results were expressed as mean±SD. Constructs indicated include: U1 87-9 (SEQ ID NO: 11); U1 87-9 SL (SEQ ID NO: 16); U1 87-9 SL broken(SEQ ID NO: 17); U1 87 mut (SEQ ID NO: 4); U1 theo_9 (SEQ ID NO: 26), U1 theo_9_1 (SEQ ID NO: 36), U1 theo_9_2 (SEQ ID NO: 37), U1 theo_9_3 (SEQ ID NO: 38), U1 theo_9_4 (SEQ ID NO: 39), U1 theo_9_5 (SEQ ID NO: 40), U1 theo_9_6 (SEQ ID NO: 41), U1 theo_9_7 (SEQ ID NO: 42), and U1 theo_9_8 (SEQ ID NO: 43).

FIG. 6a. A schematic showing the 4 copies of U1_theo_8_1 in the 3' UTR of the target gene (luciferase) (SEQ ID NO: 44).

FIG. 6b. HEK 293 were transfected with the indicated constructs, and treated with theophylline at different concentrations. Four copies of U1_theo_8_1 in the 3' UTR (SEQ ID NO: 44) yielded a 4.3-fold induction of luciferase activity at 6 mM concentration. Other constructs indicated include: U1 87-9 SL (SEQ ID NO: 16); U1 87-9 SL broken (SEQ ID NO: 17); and U1 theo_8_1 (SEQ ID NO: 27).

FIG. 7a. Schematic indicating the U1_Gua sequence at different positions in 3' UTR containing SV40 early poly(A) signal, i.e. −149 U1_Gua_1 (SEQ ID NO: 45), −110 U1_Gua_2 (SEQ ID NO: 47), and −74 U1_Gua_3 (SEQ ID NO: 49).

FIG. 7b. Schematic showing the effector region stem sequence in U1_Gua switch that sequesters the U1 site (in the presence of guanine ligand) and connects guanine aptamer. Guanine is shown as ●.

FIG. 7c. Guanine aptamer regulates U1 interference with polyadenylation in response to guanine treatment. HEK 293 cells were transfected with the indicated constructs. Constructs containing the mutant U1 site and its complementary sequence were used as control. Results were expressed as mean±SD, the induction folds are shown for each construct. Indicated sequences include: U1_Gua_1 wt (SEQ ID NO: 45); U1_Gua_1 mut (SEQ ID NO: 45); U1_Gua_2 wt (SEQ ID NO: 47); U1_Gua_2 mut (SEQ ID NO: 48); U1_Gua_3 wt (SEQ ID NO: 49); and U1_Gua_3 mut (SEQ ID NO: 50).

Figure 8:
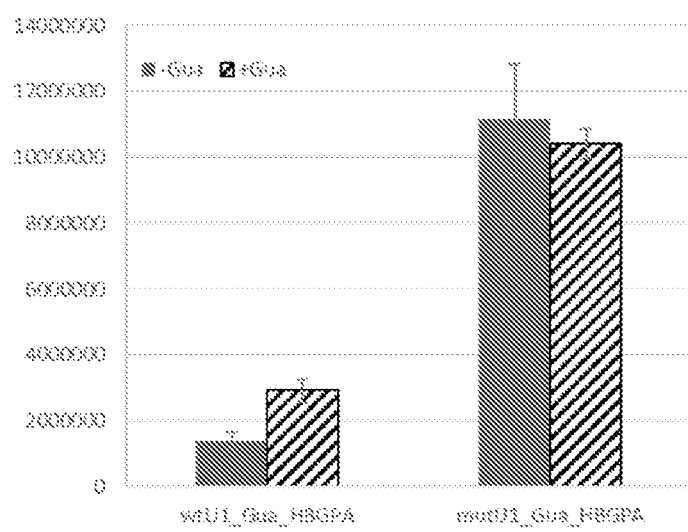

FIG. 8. U1_Gua riboswitch functions in the context of human beta globin polyA sequence. Sequences indicated include wt U1_Gua_HBGPA (SEQ ID NO: 51) and mut US_Gua_HBGPA (SEQ ID NO: 52).

DETAILED DESCRIPTION OF THE INVENTION

The invention provides polynucleotide constructs for the regulation of gene expression by aptamer-based modulation of U1 snRNP-mediated suppression of polyadenylation and methods of using the constructs to regulate gene expression in response to the presence or absence of a ligand that binds the aptamer. The polynucleotide construct contains at least one riboswitch that contains an effector region and a sensor region. The effector region contains a U1 snRNP binding site and sequence complementary to the U1 snRNP binding site such that the two sequences are capable of forming a stem that sequesters the U1 snRNP binding site thereby preventing binding of the U1 snRNP. The effector region may contain additional sequence and its complement so that the effector region stem is longer than the U1 snRNP binding site and its complementary sequence. The sensor region comprises an RNA sequence that binds a ligand, and in response to this binding alters the conformation of the effector region. In one embodiment, the sensor region comprises an aptamer. When the aptamer ligand is not present, the effector region does not form a stem. The U1 snRNP binding site is available and is bound by a U1 snRNP, which inhibits polyadenylation of the mRNA. When the aptamer ligand is present, it binds the aptamer causing the effector region to form a stem, which prevents U1 snRNP from binding the U1 binding site. The U1 snRNP is not recruited to the 3' UTR of the target gene mRNA and polyadenylation of the message occurs.

The gene regulation polynucleotide cassette refers to a recombinant DNA construct that, when incorporated into the DNA of a target gene in the 3' UTR, provides the ability to regulate expression of the target gene by aptamer/ligand mediated suppression of polyadenylation by U1 snRNP. As used herein, a polynucleotide cassette or construct is a nucleic acid (e.g., DNA or RNA) comprising elements derived from different sources (e.g., different organisms, different genes from the same organism, and the like). The polynucleotide cassette comprises a riboswitch. The riboswitch in the context of the present invention contains a sensor region (e.g., an aptamer) and an effector region that together are responsible for sensing the presence of a ligand that binds the sensor region and altering the conformation of the effector region that contains a U1 snRNP binding site and sequence that is complementary to the U1 snRNP binding site. In one embodiment, the target gene's expression is increased when the aptamer ligand is present and decreased when the ligand is absent.

Riboswitch

The term "riboswitch" as used herein refers to a regulatory segment of a RNA polynucleotide. A riboswitch in the context of the present invention contains a sensor region (e.g., an aptamer) and an effector region that together are responsible for sensing the presence of a ligand (e.g., a small molecule) and modulating the accessibility of a U1 snRNP binding site located in the effector region. In one embodiment, the riboswitch is recombinant, utilizing polynucleotides from two or more sources. The term "synthetic" as used herein in the context of a riboswitch refers to a riboswitch that is not naturally occurring. In one embodiment, the sensor and effector regions are joined by a polynucleotide linker. In one embodiment, the polynucleotide linker forms a RNA stem (i.e., a region of the RNA polynucleotide that is double-stranded).

Effector Region

The effector region of the riboswitch comprises RNA sequence that, in response to ligand binding the sensor region (e.g., an aptamer), forms a stem structure (a double-stranded region) that lowers the accessibility of a U1 snRNP binding site to the U1 snRNP. The effector region comprises a U1 snRNP binding site and sequence complimentary the U1 snRNP binding site. When the aptamer binds its ligand, the effector region forms a stem and thus sequesters the U1 snRNP binding site from binding a U1 snRNP. Under certain conditions (for example, when the aptamer is not bound to its ligand), the effector region is in a context that provides access to the U1 snRNP binding site, allowing U1 snRNP to bind the mRNA and inhibit polyadenylation leading to degradation of the message.

The U1 snRNP binding site can be any polynucleotide sequence that is capable of binding the U1 snRNP, thereby recruiting the U1 snRNP to the 3' UTR of a target gene and suppressing polyadenylation of the target gene message. In one embodiment, the U1 snRNP binding site (also referred to herein as the "U1 binding site" or "U1 site") is the consensus site CAGGTAAGTA (CAGGUAAGUA when in the mRNA). In some embodiments, the U1 snRNP binding site is a variation of this consensus sequence, including for example sequences that are shorter or have one or more nucleotides changed from the consensus sequence. In one embodiment, the U1 snRNP binding site contains the sequence CAGGTAAG. In some embodiments, the binding site is encoded by the sequence selected from CAGGTAAGTA, CAGGTAAGT, and CAGGTAAG. The U1 snRNP binding site can be any 5' splice site from a gene, e.g., the 5' splice site from human DHFR exon 2 (see Examples 7 and 8).

The stem portion of the effector region should be of a sufficient length (and GC content) to inhibit U1 snRNP binding the U1 snRNP binding site upon ligand binding the aptamer, while also allowing access to the U1 snRNP binding site when the ligand is not present in sufficient quantities. In embodiments of the invention, the stem portion of the effector region comprises stem sequence in addition to U1 snRNP binding site and its complementary sequence. In embodiments of the invention, this additional stem sequence comprises sequence from the aptamer stem. The length and sequence of the stem portion can be modified using known techniques in order to identify stems that allow acceptable background expression of the target gene when no ligand is present and acceptable expression levels of the target gene when the ligand is present. If the stem is, for example, too long it may hide access to the U1 snRNP binding site in the presence or absence of ligand. If the stem is too short, it may not form a stable stem capable of sequestering the U1 snRNP binding site, in which case U1 snRNP will bind and inhibit polyadenylation of the message (leading to degradation of the target gene mRNA) in the presence or absence of ligand. In one embodiment, the total length of the effector region stem is between about 7 base pairs to about 20 base pairs. In some embodiments, the length of the stem is between about 8 base pairs to about 11 base pairs. In some embodiments, the length of the stem is 8 base pairs to 11 base pairs. In addition to the length of the stem, the GC base pair content of the stem can be altered to modify the stability of the stem.

In some embodiments, the effector region stem contains one or more mismatched nucleotides that do not base pair with the complementary portion of the effector region stem.

Aptamer/Ligand

In one embodiment, the sensor region comprises an aptamer. The term "aptamer" as used herein refers to an RNA polynucleotide that specifically binds to a ligand. The term "ligand" refers to a molecule that is specifically bound by an aptamer. In one embodiment, the ligand is a low molecular weight (less than about 1,000 Daltons) molecule including, for example, lipids, monosaccharides, second messengers, co-factors, metal ions, other natural products and metabolites, nucleic acids, as well as most therapeutic drugs. In one embodiment, the ligand is a polynucleotide with two or more nucleotide bases.

In one embodiment, the ligand is selected from the group consisting of 8-azaguanine, adenosine 5'-monophosphate monohydrate, amphotericin B, avermectin B1, azathioprine, chlormadinone acetate, mercaptopurine, moriciziine hydrochloride, N6-methyladenosine, nadide, progesterone, promazine hydrochloride, pyrvinium pamoate, sulfaguanidine, testosterone propionate, thioguanosine, tyloxapol and vorinostat.

Aptamer ligands can also be cell endogenous components that increase significantly under specific physiological/pathological conditions, such as oncogenic transformation—these may include second messenger molecules such as GTP or GDP, calcium; fatty acids, or fatty acids that are incorrectly metabolized such as 13-HODE in breast cancer (Flaherty, J T et al., *Plos One*, Vol. 8, e63076, 2013, incorporated herein by reference); amino acids or amino acid metabolites; metabolites in the glycolysis pathway that usually have higher levels in cancer cells or in normal cells in metabolic diseases; and cancer-associated molecules such as Ras or mutant Ras protein, mutant EGFR in lung cancer, indoleamine-2,3-dioxygenase (IDO) in many types of cancers. Endogenous ligands include progesterone metabolites in breast cancer as disclosed by J P Wiebe (Endocrine-Related *Cancer* (2006) 13:717-738, incorporated herein by reference). Endogenous ligands also include metabolites with increased levels resulting from mutations in key metabolic enzymes in kidney cancer such as lactate, glutathione, kynurenine as disclosed by Minton, D R and Nanus, D M (Nature Reviews, Urology, Vol. 12, 2005, incorporated herein by reference).

Aptamers have binding regions that are capable of forming complexes with an intended target molecule (i.e., the ligand). The specificity of the binding can be defined in terms of the comparative dissociation constants (Kd) of the aptamer for its ligand as compared to the dissociation constant of the aptamer for unrelated molecules. Thus, the ligand is a molecule that binds to the aptamer with greater affinity than to unrelated material. Typically, the Kd for the aptamer with respect to its ligand will be at least about 10-fold less than the Kd for the aptamer with unrelated molecules. In other embodiments, the Kd will be at least about 20-fold less, at least about 50-fold less, at least about 100-fold less, and at least about 200-fold less. An aptamer will typically be between about 15 and about 200 nucleotides in length. More commonly, an aptamer will be between about 30 and about 100 nucleotides in length.

The aptamers that can be incorporated as part of the riboswitch can be a naturally occurring aptamer, or modifications thereof, or aptamers that are designed de novo and/or screened through systemic evolution of ligands by exponential enrichment (SELEX) or other screening methods. Examples of aptamers that bind small molecule ligands include, but are not limited to theophylline, dopamine, sulforhodamine B, cellobiose, kanamycin A, lividomycin, tobramycin, neomycin B, viomycin, chloramphenicol, streptomycin, cytokines, cell surface molecules, and metabolites. For a review of aptamers that recognize small molecules, see, e.g., Famulok, *Science* 9:324-9 (1999) and McKeague, M. & DeRosa, M. C. J. *Nuc. Aci.* 2012 (both of which are incorporated herein by reference). In another embodiment, the aptamer is a complementary polynucleotide.

Methods for Identifying Aptamer/Ligand

In one embodiment, the aptamer is designed to bind a particular small molecule ligand. Methods for designing and selecting aptamers that bind particular ligands are disclosed in 62/370,599, incorporated herein by reference. Other methods for screening aptamers include, for example, SELEX. Methods for designing aptamers that selectively bind a small molecule using SELEX are disclosed in, e.g., U.S. Pat. Nos. 5,475,096, 5,270,163, and Abdullah Ozer, et al. *Nuc. Aci.* 2014, which are incorporated herein by reference. Modifications of the SELEX process are described in U.S. Pat. Nos. 5,580,737 and 5,567,588, which are incorporated herein by reference.

Selection techniques for identifying aptamers generally involve preparing a large pool of DNA or RNA molecules of the desired length that contain a region that is randomized or mutagenized. For example, an oligonucleotide pool for aptamer selection might contain a region of 20-100 randomized nucleotides flanked by regions of defined sequence that are about 15-25 nucleotides long and useful for the binding of PCR primers. The oligonucleotide pool is amplified using standard PCR techniques, or other means that allow amplification of selected nucleic acid sequences. The DNA pool may be transcribed in vitro to produce a pool of RNA transcripts when an RNA aptamer is desired. The pool of RNA or DNA oligonucleotides is then subjected to a selection based on their ability to bind specifically to the desired ligand. Selection techniques include, for example, affinity chromatography, although any protocol which will allow selection of nucleic acids based on their ability to bind specifically to another molecule may be used. Selection techniques for identifying aptamers that bind small molecules and function within a cell may involve cell based screening methods. In the case of affinity chromatography, the oligonucleotides are contacted with the target ligand that has been immobilized on a substrate in a column or on magnetic beads. The oligonucleotide is preferably selected for ligand binding in the presence of salt concentrations, temperatures, and other conditions which mimic normal physiological conditions. Oligonucleotides in the pool that bind to the ligand are retained on the column or bead, and nonbinding sequences are washed away. The oligonucleotides that bind the ligand are then amplified (after reverse transcription if RNA transcripts were utilized) by PCR (usually after elution). The selection process is repeated on the selected sequences for a total of about three to ten iterative rounds of the selection procedure. The resulting oligonucleotides are then amplified, cloned, and sequenced using standard procedures to identify the sequences of the oligonucleotides that are capable of binding the target ligand. Once an aptamer sequence has been identified, the aptamer may be further optimized by performing additional rounds of selection starting from a pool of oligonucleotides comprising a mutagenized aptamer sequence.

In vivo aptamer screening may be used following one or more rounds of in vitro selection (e.g., SELEX). For example, Konig, J. et al. (*RNA*. 2007, 13(4):614-622, incorporated herein by reference) describe combining SELEX and a yeast three-hybrid system for in vivo selection of aptamer.

Target Genes

The gene regulation cassette of the present invention is a platform that can be used to regulate the expression of any target gene that can be expressed in a target cell, tissue or organism. The term "target gene" refers to a polynucleotide that is introduced into a cell and is capable of being transcribed into RNA and translated and/or expressed under appropriate conditions. Alternatively, the target gene is endogenous to the target cell and the gene regulation cassette of the present invention is positioned into the target gene (for example into the 5' or 3' UTR of an endogenous target gene). An example of a target gene is a polynucleotide encoding a therapeutic polypeptide. In another embodiment, the target gene encodes an RNA such as a miRNA, rRNA, small or long noncoding RNAs, short hairpin RNA (shRNA) and any other regulatory RNAs. In one embodiment, the target gene is exogenous to the cell in which the recombinant DNA construct is to be transcribed. In another embodiment, the target gene is endogenous to the cell in which the recombinant DNA construct is to be transcribed.

The target gene according to the present invention may be a gene encoding a protein, or a sequence encoding a non-protein coding RNA. The target gene may be, for example, a gene encoding a structural protein, an enzyme, a cell signaling protein, a mitochondrial protein, a zinc finger protein, a hormone, a transport protein, a growth factor, a cytokine, an intracellular protein, an extracellular protein, a transmembrane protein, a cytoplasmic protein, a nuclear protein, a receptor molecule, an RNA binding protein, a DNA binding protein, a transcription factor, translational machinery, a channel protein, a motor protein, a cell adhesion molecule, a mitochondrial protein, a metabolic enzyme, a kinase, a phosphatase, exchange factors, a chaperone protein, and modulators of any of these. In embodiments, the target gene encodes erythropoietin (Epo), human growth hormone (hGH), transcription activator-like effector nucleases (TALEN), human insulin, CRISPR associated protein 9 (cas9), or an immunoglobulin (or portion thereof), including, e.g., a therapeutic antibody.

Expression Constructs

The present invention contemplates the use of a recombinant vector for introduction into target cells of a polynucleotide encoding a target gene and containing the gene regulation cassette described herein. In many embodiments, the recombinant DNA construct of this invention includes additional DNA elements including DNA segments that provide for the replication of the DNA in a host cell and expression of the target gene in that cell at appropriate levels. The ordinarily skilled artisan appreciates that expression control sequences (promoters, enhancers, and the like) are selected based on their ability to promote expression of the target gene in the target cell. "Vector" means a recombinant plasmid, yeast artificial chromosome (YAC), mini chromosome, DNA mini-circle or virus (including virus derived sequences) that comprises a polynucleotide to be delivered into a host cell, either in vitro or in vivo. In one embodiment, the recombinant vector is a viral vector or a combination of multiple viral vectors.

Viral vectors for the aptamer-mediated expression of a target gene in a target cell, tissue, or organism are known in the art and include adenoviral (AV) vectors, adeno-associated virus (AAV) vectors, retroviral and lentiviral vectors, and Herpes simplex type 1 (HSV1) vectors.

Adenoviral vectors include, for example, those based on human adenovirus type 2 and human adenovirus type 5 that have been made replication defective through deletions in the E1 and E3 regions. The transcriptional cassette can be inserted into the E1 region, yielding a recombinant E1/E3-deleted AV vector. Adenoviral vectors also include helper-dependent high-capacity adenoviral vectors (also known as high-capacity, "gutless" or "gutted" vectors), which do not contain viral coding sequences. These vectors, contain the cis-acting elements needed for viral DNA replication and packaging, mainly the inverted terminal repeat sequences (ITR) and the packaging signal (Ψ). These helper-dependent AV vector genomes have the potential to carry from a few hundred base pairs up to approximately 36 kb of foreign DNA.

Recombinant adeno-associated virus "rAAV" vectors include any vector derived from any adeno-associated virus serotype, including, without limitation, AAV-1, AAV-2, AAV-3, AAV-4, AAV-5, AAV-7 and AAV-8, AAV-9, AAV-10, and the like. rAAV vectors can have one or more of the AAV wild-type genes deleted in whole or in part, preferably the Rep and/or Cap genes, but retain functional flanking ITR sequences. Functional ITR sequences are retained for the rescue, replication, packaging and potential chromosomal integration of the AAV genome. The ITRs need not be the wild-type nucleotide sequences, and may be altered (e.g., by the insertion, deletion or substitution of nucleotides) so long as the sequences provide for functional rescue, replication and packaging.

Alternatively, other systems such as lentiviral vectors can be used in embodiments of the invention. Lentiviral-based systems can transduce non-dividing as well as dividing cells making them useful for applications targeting, for examples, the non-dividing cells of the CNS. Lentiviral vectors are derived from the human immunodeficiency virus and, like that virus, integrate into the host genome providing the potential for long-term gene expression.

Polynucleotides, including plasmids, YACs, minichromosomes and minicircles, carrying the target gene containing the gene regulation cassette can also be introduced into a cell or organism by nonviral vector systems using, for example, cationic lipids, polymers, or both as carriers. Conjugated poly-L-lysine (PLL) polymer and polyethylenimine (PEI) polymer systems can also be used to deliver the vector to cells. Other methods for delivering the vector to cells includes hydrodynamic injection and electroporation and use of ultrasound, both for cell culture and for organisms. For a review of viral and non-viral delivery systems for gene delivery see Nayerossadat, N. et al. (*Adv Biomed Res.* 2012; 1:27; incorporated herein by reference).

Methods of Modulating Expression of a Target Gene

In one aspect, this invention provides a method of modulating expression of a target gene (e.g., a therapeutic gene), by (a) inserting the gene regulation cassette of the present invention into the 3' UTR of a target gene; (b) introducing the target gene comprising the gene regulation cassette into a cell; and (c) exposing the cell to a ligand that binds the aptamer. In one embodiment, the ligand is a small molecule. In aspects, expression of the target gene in target cells confers a desired property to a cell into which it was introduced, or otherwise leads to a desired therapeutic outcome.

In one embodiment, one or more gene regulation cassettes are inserted into the 3' untranslated region of the target gene. In one embodiment, a single gene regulation cassette is inserted into the 3' UTR of a target gene. In other embodiments 2, 3, 4, or more gene regulation cassettes are inserted in the target gene. In one embodiment, two gene regulation cassettes are inserted into the target gene. When multiple gene regulation cassettes are inserted into a target gene, they each can contain the same aptamer such that a single ligand can be used to modulate ribonuclease cleavage of the multiple cassettes and thereby modulate target gene expression. In other embodiments, multiple gene regulation cassettes are inserted into a target gene, each can contain a different aptamer so that exposure to multiple different small molecule ligands modulates target gene expression. In other embodiments, multiple gene regulation cassettes are inserted into a target gene, each containing different ribonuclease substrate sequences. This may be useful in reducing recombination and improving ease of incorporation into viral vectors.

The polynucleotide cassettes of the present invention are effective at modulating target gene expression when the polynucleotide cassette is located in the 3' UTR of the target gene at any location upstream (5') of the polyadenylation signal (e.g., AATAAA). The polynucleotide cassette is also effective at modulating target gene expression by blocking polyadenylation when different poly(A) signal sequences are present, for example the SV40 early versus late poly(A) signals (see, e.g., Examples 4-6, 8). In one embodiment, the at least one polynucleotide cassette of the present invention is inserted about 87 or about 140 nucleotides 5' of the polyadenylation sequence. In one embodiment, a polynucleotide cassette of the present invention is inserted at, or near, both locations. In other embodiments, a polynucleotide cassette is inserted at one or more of about 74, about 110, or about 149 nucleotides 5' of the polyadenylation signal.

The polynucleotide cassette of the present invention can be used in combination with other mechanisms for the regulation of expression of the target gene. In one embodiment, a polynucleotide cassette of the present invention is used in combination with a gene regulation cassette that modulates target gene expression by aptamer-mediated regulation of alternative splicing as described in WO 2016/126747, incorporated herein by reference.

Methods of Treatment and Pharmaceutical Compositions

One aspect of the invention provides a method of regulating the level of a therapeutic protein delivered by gene therapy. In this embodiment, the "target gene" may encode the therapeutic protein. The "target gene" may encode a protein that is endogenous or exogenous to the cell.

The therapeutic gene sequence containing the regulatory cassette with aptamer-driven riboswitch is delivered to target cells in vitro or ex vivo, e.g., by a vector. The cell specificity of the "target gene" may be controlled by promoter or other elements within the vector. Delivery of the vector construct containing the target gene and the polynucleotide cassette, and the transfection of the target tissues resulting in stable transfection of the regulated target gene, is often the first step in producing the therapeutic protein.

However, due to the presence of the regulatory cassette within the target gene sequence, the target gene is not expressed at significant levels, i.e., it is in the "off state" in the absence of the specific ligand that binds to the aptamer contained within in the regulatory cassette riboswitch. Only when the aptamer specific ligand is administered (or otherwise present in sufficient quantities) is the target gene expression activated.

The delivery of the vector construct containing the target gene and the delivery of the activating ligand generally are separated in time. The delivery of the activating ligand will control when the target gene is expressed, as well as the level of protein expression. The ligand may be delivered by a number of routes including, but not limited to, oral, intramuscular (IM), intravenous (IV), intraocular, or topically.

The timing of delivery of the ligand will depend on the requirement for activation of the target gene. For example, if the therapeutic protein encoded by the target gene is required constantly, an oral small molecule ligand may be delivered daily, or multiple times a day, to ensure continual activation of the target gene, and thus continual expression of the therapeutic protein. If the target gene has a long acting effect, the inducing ligand may be dosed less frequently.

This invention allows the expression of the therapeutic transgene to be controlled temporally, in a manner determined by the temporal dosing of the ligand specific to the aptamer within the riboswitch of the regulatory polynucleotide cassette. The increased expression of the therapeutic transgene only on ligand administration, increases the safety of a gene therapy treatment by allowing the target gene to be off in the absence of the ligand.

Different aptamers can be used to allow different ligands to activate target genes. In certain embodiments of the invention, each therapeutic gene containing a regulatory cassette will have a specific aptamer within the cassette that will be activated by a specific small molecule. This means that each therapeutic gene can be activated only by the ligand specific to the aptamer housed within it. In these embodiments, each ligand will only activate one therapeutic gene. This allows for the possibility that several different "target genes" may be delivered to one individual and each will be activated on delivery of the specific ligand for the aptamer contained within the regulatory cassette housed in each target gene.

This invention allows any therapeutic protein whose gene can be delivered to the body (such as erythropoietin (EPO) or a therapeutic antibody) to be produced by the body when the activating ligand is delivered. This method of therapeutic protein delivery may replace the manufacture of such therapeutic proteins outside of the body which are then injected or infused, e.g., antibodies used in cancer or to block inflammatory or autoimmune disease. The body containing the regulated target gene becomes the biologics manufacturing factory, which is switched on when the gene-specific ligand is administered.

Dosing levels and timing of dosing of a therapeutic protein may be important to therapeutic effect. For example, in the delivery of AVASTIN (anti-VEGF antibody) for cancer. The present invention increases the ease of dosing in response to monitoring for therapeutic protein levels and effects.

In one embodiment, the target gene may encode a nuclease that can target and edit a particular DNA sequence. Such nucleases include Cas9, zinc finger containing nucleases, or TALENs. In the case of these nucleases, the nuclease protein may be required for only a short period of time that is sufficient to edit the target endogenous genes. However, if an unregulated nuclease gene is delivered to the body, this protein may be present for the rest of the life of the cell. In the case of nucleases, there is an increasing risk of off-target editing the longer the nuclease is present. Regulation of expression of such proteins has a significant safety advantage. In this case, vector containing the nuclease target gene containing a regulatory cassette could be delivered to the appropriate cells in the body. The target gene is in the "off"

state in the absence of the cassette-specific ligand, so no nuclease is produced. Only when the activating ligand is administered, is the nuclease produced. When sufficient time has elapsed allowing sufficient editing to occur, the ligand will be withdrawn and not administered again. Thus, the nuclease gene is thereafter in the "off" state and no further nuclease is produced and editing stops. This approach may be used to correct genetic conditions, including a number of inherited retinopathies such as LCA10 caused by mutations in CEP290 and Stargardt's Disease caused by mutations in ABCA4.

Administration of a regulated target gene encoding a therapeutic protein which is activated only on specific ligand administration may be used to regulate therapeutic genes to treat many different types of diseases, e.g., cancer with therapeutic antibodies, immune disorders with immune modulatory proteins or antibodies, metabolic diseases, rare diseases such as PNH with anti-C5 antibodies or antibody fragments as the regulated gene, or ocular angiogenesis with therapeutic antibodies, and dry AMD with immune modulatory proteins.

A wide variety of specific target genes, allowing for the treatment of a wide variety of specific diseases and conditions, are suitable for use in the present invention. For example, insulin or an insulin analog (preferably human insulin or an analog of human insulin) may be used as the target gene to treat type I diabetes, type II diabetes, or metabolic syndrome; human growth hormone may be used as the target gene to treat children with growth disorders or growth hormone-deficient adults; erythropoietin (preferably human erythropoietin) may be used as the target gene to treat anemia due to chronic kidney disease, anemia due to myelodysplasia, or anemia due to cancer chemotherapy.

The present invention may be especially suitable for treating diseases caused by single gene defects such as cystic fibrosis, hemophilia, muscular dystrophy, thalassemia, or sickle cell anemia. Thus, human ($\beta$-, $\gamma$-, $\delta$-, or $\zeta$-globin may be used as the target gene to treat $\beta$-thalassemia or sickle cell anemia; human Factor VIII or Factor IX may be used as the target gene to treat hemophilia A or hemophilia B.

The ligands used in the present invention are generally combined with one or more pharmaceutically acceptable carriers to form pharmaceutical compositions suitable for administration to a patient. Pharmaceutically acceptable carriers include solvents, binders, diluents, disintegrants, lubricants, dispersion media, coatings, antibacterial and antifungal agents, isotonic and absorption delaying agents, and the like, generally used in the pharmaceutical arts. Pharmaceutical compositions may be in the form of tablets, pills, capsules, troches, and the like, and are formulated to be compatible with their intended route of administration. Examples of routes of administration include parenteral, e.g., intravenous, intradermal, intranasal, subcutaneous, oral, inhalation, transdermal (topical), transmucosal, and rectal.

The pharmaceutical compositions comprising ligands are administered to a patient in a dosing schedule such that an amount of ligand sufficient to desirably regulate the target gene is delivered to the patient. When the ligand is a small molecule and the dosage form is a tablet, capsule, or the like, preferably the pharmaceutical composition comprises from 0.1 mg to 10 g of ligand; from 0.5 mg to 5 g of ligand; from 1 mg to 1 g of ligand; from 2 mg to 750 mg of ligand; from 5 mg to 500 mg of ligand; or from 10 mg to 250 mg of ligand.

The pharmaceutical compositions may be dosed once per day or multiple times per day (e.g., 2, 3, 4, 5, or more times per day). Alternatively, pharmaceutical compositions may be dosed less often than once per day, e.g., once every 2, 3, 4, 5, 6, 7, 8, 9, 10, 11, 12, 13, or 14 days, or once a month or once every few months. In some embodiments of the invention, the pharmaceutical compositions may be administered to a patient only a small number of times, e.g., once, twice, three times, etc.

The present invention provides a method of treating a patient in need of increased expression of a therapeutic protein encoded by a target gene, the method comprising administering to the patient a pharmaceutical composition comprising a ligand for an aptamer, where the patient previously had been administered a recombinant DNA comprising the target gene, where the target gene contains a gene regulation cassette of the present invention that provides the ability to regulate expression of the target gene by the ligand of the aptamer by alternative splicing of pre-mRNA of the target gene, thereby increasing expression of the therapeutic protein.

Articles of Manufacture and Kits

Also provided are kits or articles of manufacture for use in the methods described herein. In aspects, the kits comprise the compositions described herein (e.g., for compositions for delivery of a vector comprising the target gene containing the gene regulation cassette) in suitable packaging. Suitable packaging for compositions (such as ocular compositions for injection) described herein are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The present invention also provides kits comprising compositions described herein and may further comprise instruction(s) on methods of using the composition, such as uses described herein. The kits described herein may further include other materials desirable from a commercial and user standpoint, including other buffers, diluents, filters, needles, syringes, and package inserts with instructions for performing the administration, including e.g., any methods described herein. For example, in some embodiments, the kit comprises rAAV for expression of the target gene comprising the gene regulation cassette of the present invention, a pharmaceutically acceptable carrier suitable for injection, and one or more of: a buffer, a diluent, a filter, a needle, a syringe, and a package insert with instructions for performing the injections. In some embodiments, the kit is suitable for intraocular injection, intramuscular injection, intravenous injection and the like.

"Homology" and "homologous" as used herein refer to the percent of identity between two polynucleotide sequences or between two polypeptide sequences. The correspondence between one sequence to another can be determined by techniques known in the art. For example, homology can be determined by a direct comparison of two polypeptide molecules by aligning the sequence information and using readily available computer programs. Two polynucleotide or two polypeptide sequences are "substantially homologous" to each other when, after optimally aligned with appropriate insertions or deletions, at least about 80%, at least about 85%, at least about 90%, and at least about 95% of the nucleotides or amino acids, respectively, match over a defined length of the molecules, as determined using the methods above.

"Percent sequence identity" with respect to a reference polypeptide or nucleic acid sequence is defined as the percentage of amino acid residues or nucleotides in a candidate sequence that are identical with the amino acid residues or nucleotides in the reference polypeptide or nucleic acid sequence, after aligning the sequences and introducing gaps, if necessary, to achieve the maximum percent sequence identity. Alignment for purposes of determining percent amino acid or nucleic acid sequence identity can be achieved in ways known to the ordinarily-skilled artisan, for example, using publicly available computer software programs including BLAST, BLAST-2, ALIGN or Megalign (DNASTAR) software.

The term "polynucleotide" or "nucleic acid" as used herein refers to a polymeric form of nucleotides of any length, either ribonucleotides or deoxyribonucleotides. Thus, this term includes, but is not limited to, single-, double- or multi- stranded DNA or RNA, genomic DNA, cDNA, DNA-RNA hybrids, or a polymer comprising purine and pyrimidine bases, or other natural, chemically or biochemically modified, non-natural, or derivatized nucleotide bases.

"Heterologous" or "exogenous" means derived from a genotypically distinct entity from that of the rest of the entity to which it is compared or into which it is introduced or incorporated. For example, a polynucleotide introduced by genetic engineering techniques into a different cell type is a heterologous polynucleotide (and, when expressed, can encode a heterologous polypeptide). Similarly, a cellular sequence (e.g., a gene or portion thereof) that is incorporated into a viral vector is a heterologous nucleotide sequence with respect to the vector.

The below table contains a listing of the DNA sequences of the constructs described herein as well as other sequences as described. The U1 binding site and its mutant sequence are in bold lower case letters; the stem-loop structure (SL) is in underlined lower case letters; aptamer sequences are in wave underlined lower case letters; poly(A) signal sequence is in thick underlined lower case letters; and coding sequences for luciferase genes are in upper case letters.

| SEQ ID NO.: | Description | Sequence |
| --- | --- | --- |
| 1 | Consensus U1 binding site | CAGGTAAGTA |
| 2 | Mutant U1 binding site | CATGGAACTA |
| 3 | U1-87 wt in pRL-SV40 | TCAAATCGTTCGTTGAGCGAGTTCTCAAAAATGAA CAATAAttctagagcggccgcttcgagcagacatgataagatacattgatgagt ttggacaaaccaggtaagtacaactagaatgcagtgaaaaaaatgctttatttgtgaa atttgtgatgctattgctttatttgtaaccattataagctgcaataaacaagttaacaacaa c |
| 4 | U1-87 mut in pRL-SV40 | TCAAATCGTTCGTTGAGCGAGTTCTCAAAAATGAA CAATAAttctagagcggccgcttcgagcagacatgataagatacattgatgagt ttggacaaaccatggaactacaactagaatgcagtgaaaaaaatgctttatttgtgaa atttgtgatgctattgctttatttgtaaccattataagctgcaataaacaagttaacaacaa c |
| 5 | U1-140 wt in pRL-SV40 | TCAAATCGTTCGTTGAGCGAGTTCTCAAAAATGAA CAATAAttctagacaggtaagtagcggccgcttcgagcagacatgataagat acattgatgagtttggacaaaccacaactagaatgcagtgaaaaaaatgctttatttgt gaaatttgtgatgctattgctttatttgtaaccattataagctgcaataaacaagttaaca acaac |
| 6 | U1-140 mut in pRL-SV40 | TCAAATCGTTCGTTGAGCGAGTTCTCAAAAATGAA CAATAAttctagacatggaactagcggccgcttcgagcagacatgataagat acattgatgagtttggacaaaccacaactagaatgcagtgaaaaaaatgctttatttgt gaaatttgtgatgctattgctttatttgtaaccattataagctgc<u>aataaa</u>caagttaaca acaac |
| 7 | 2xU1-140 wt in pRL-SV40 | TCAAATCGTTCGTTGAGCGAGTTCTCAAAAATGAA CAATAAttctagacaggtaagtaaccaaacaggtaagtagcggccgcttcg agcagacatgataagatacattgatgagtttggacaaaccacaactagaatgcagtg aaaaaaatgctttatttgtgaaatttgtgatgctattgctttatttgtaaccattataagctg c<u>aataaa</u>caagttaacaacaac |
| 8 | 2xU1-140 mut in pRL-SV40 | TCAAATCGTTCGTTGAGCGAGTTCTCAAAAATGAA CAATAAttctagacatggaactaaccaaacatggaactagcggccgcttcga gcagacatgataagatacattgatgagtttggacaaaccacaactagaatgcagtga aaaaaatgctttatttgtgaaatttgtgatgctattgctttatttgtaaccattataagctgc <u>aataaa</u>caagttaacaacaac |
| 9 | 3xU1-140 wt in pRL-SV40 | TCAAATCGTTCGTTGAGCGAGTTCTCAAAAATGAA CAATAAttctagacaggtaagtaaccaaacaggtaagtaaccaaacaggta agtagcggccgcttcgagcagacatgataagatacattgatgagtttggacaaacca caactagaatgcagtgaaaaaaatgctttatttgtgaaatttgtgatgctattgctttattt gtaaccattataagctgcAATAAAcaagttaacaacaac |
| 10 | 3xU1_140 mut in pRL-SV40 | TCAAATCGTTCGTTGAGCGAGTTCTCAAAAATGAA CAATAAttctagacatggaactaaccaaacatggaactaaccaaacatgga actagcggccgcttcgagcagacatgataagatacattgatgagtttggacaaacca caactagaatgcagtgaaaaaaatgctttatttgtgaaatttgtgatgctattgctttattt gtaaccattataagctgcAATAAAcaagttaacaacaac |

| SEQ ID NO.: | Description | Sequence |
|---|---|---|
| 11 | 87-9 in pRL-SV40 | TCAAATCGTTCGTTGAGCGAGTTCTCAAAAATGAA CAATAAttctagagcggccgcttcgagcagacatgataagatacattgatgagt ttggacaaaccaggtaagtcaactagaatgcagtgaaaaaaatgctttatttgtgaaa tttgtgatgctattgctttatttgtaaccattataagctgc<u>aataaa</u>caagttaacaacaac |
| 12 | 87-8 in pRL-SV40 | TCAAATCGTTCGTTGAGCGAGTTCTCAAAAATGAA CAATAAttctagagcggccgcttcgagcagacatgataagatacattgatgagt ttggacaaaccaggtaagcaactagaatgcagtgaaaaaaatgctttatttgtgaaat tgtgatgctattgctttatttgtaaccattataagctgc<u>aataaa</u>caagttaacaacaac |
| 13 | 87-7 in pRL-SV40 | TCAAATCGTTCGTTGAGCGAGTTCTCAAAAATGAA CAATAAttctagagcggccgcttcgagcagacatgataagatacattgatgagt ttggacaaaccaggtaacaactagaatgcagtgaaaaaaatgctttatttgtgaaattt gtgatgctattgctttatttgtaaccattataagctgc<u>aataaa</u>caagttaacaacaac |
| 14 | 87-6 in pRL-SV40 | TCAAATCGTTCGTTGAGCGAGTTCTCAAAAATGAA CAATAAttctagagcggccgcttcgagcagacatgataagatacattgatgagt ttggacaaaccaggtacaactagaatgcagtgaaaaaaatgctttatttgtgaaatttg tgatgctattgctttatttgtaaccattataagctgc<u>aataaa</u>caagttaacaacaac |
| 15 | 87-5 in pRL-SV40 | TCAAATCGTTCGTTGAGCGAGTTCTCAAAAATGAA CAATAAttctagagcggccgcttcgagcagacatgataagatacattgatgagt ttggacaaaccaggtcaactagaatgcagtgaaaaaaatgctttatttgtgaaatttgt gatgctattgctttatttgtaaccattataagctgc<u>aataaa</u>caagttaacaacaac |
| 16 | U1 87-9 SL in pRL-SV40 | TCAAATCGTTCGTTGAGCGAGTTCTCAAAAATGAA CAATAAttctagagcggccgcttcgagcagacatgataagatacattgatgagt ttggacaaaccaaa<u>cccaggtaagttaccgaaaggtaacttacctggg</u>caactagaa tgcagtgaaaaaaatgctttatttgtgaaatttgtgatgctattgctttatttgtaaccatta taagctgc<u>aataaa</u>caagttaacaacaac |
| 17 | U1 87-9 SL broken in pRL-SV40 | TCAAATCGTTCGTTGAGCGAGTTCTCAAAAATGAA CAATAAttctagagcggccgcttcgagcagacatgataagatacattgatgagt ttggacaaaccaaa<u>cccaggtaagttaccgaaaaaaacaaacaaaaaa</u>caactaga atgcagtgaaaaaaatgctttatttgtgaaatttgtgatgctattgctttatttgtaaccatt ataagctgc<u>aataaa</u>caagttaacaacaac |
| 18 | U1_theo_1 in pRL-SV40 | TCAAATCGTTCGTTGAGCGAGTTCTCAAAAATGAA CAATAAttctagagcggccgcttcgagcagacatgataagatacattgatgagt ttggacaaaccaaa<u>cccaggtaagttaccggcgataccagccgaaaggcccttggc agcgtc</u>ggtaacttacctgggcaactagaatgcagtgaaaaaaatgctttatttgtgaa atttgtgatgctattgctttatttgtaaccattataagctgc<u>aataaa</u>caagttaacaacaa c |
| 19 | U1_theo_2 in pRL-SV40 | TCAAATCGTTCGTTGAGCGAGTTCTCAAAAATGAA CAATAAttctagagcggccgcttcgagcagacatgataagatacattgatgagt ttggacaaaccaaa<u>cccaggtaagttacggcgataccagccgaaaggcccttggca gcgt</u>gtaacttacctgggcaactagaatgcagtgaaaaaaatgctttatttgtgaaat tgtgatgctattgctttatttgtaaccattataagctgc<u>aataaa</u>caagttaacaacaac |
| 20 | U1_theo_3 in pRL-SV40 | TCAAATCGTTCGTTGAGCGAGTTCTCAAAAATGAA CAATAAttctagagcggccgcttcgagcagacatgataagatacattgatgagt ttggacaaaccaaa<u>cccaggtaagttacgcgataccagccgaaaggcccttggcag cgt</u>gtaacttacctgggcaactagaatgcagtgaaaaaaatgctttatttgtgaaatttg tgatgctattgctttatttgtaaccattataagctgc<u>aataaa</u>caagttaacaacaac |
| 21 | U1_theo_4 in pRL-SV40 | TCAAATCGTTCGTTGAGCGAGTTCTCAAAAATGAA CAATAAttctagagcggccgcttcgagcagacatgataagatacattgatgagt ttggacaaaccaaa<u>cccaggtaagttagcgataccagccgaaaggcccttggcagc gt</u>taacttacctgggcaactagaatgcagtgaaaaaaatgctttatttgtgaaatttgtg atgctattgctttatttgtaaccattataagctgc<u>aataaa</u>caagttaacaacaac |
| 22 | U1_theo_5 in pRL-SV40 | TCAAATCGTTCGTTGAGCGAGTTCTCAAAAATGAA CAATAAttctagagcggccgcttcgagcagacatgataagatacattgatgagt ttggacaaaccaaa<u>cccaggtaagttacgataccagccgaaaggcccttggcagcg taacttacctggg</u>caactagaatgcagtgaaaaaaatgctttatttgtgaaatttgtgat gctattgctttatttgtaaccattataagctgc<u>aataaa</u>caagttaacaacaac |
| 23 | U1_theo_6 in pRL-SV40 | TCAAATCGTTCGTTGAGCGAGTTCTCAAAAATGAA CAATAAttctagagcggccgcttcgagcagacatgataagatacattgatgagt ttggacaaaccaaa<u>cccaggtaagttcgataccagccgaaaggcccttggcagcga acttacctggg</u>caactagaatgcagtgaaaaaaatgctttatttgtgaaatttgtgatgc tattgctttatttgtaaccattataagctgc<u>aataaa</u>caagttaacaacaac |

-continued

| SEQ ID NO.: | Description | Sequence |
|---|---|---|
| 24 | U1_theo_7 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagttgataccagccgaaaggcccttggcagcaac ttacctgggcaactagaatgcagtgaaaaaaatgctttatttgtgaaatttgtgatgctat tgctttatttgtaaccattataagctgcaataaacaagttaacaacaac |
| 25 | U1_theo_8 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtgataccagccgaaaggcccttggcagcactt acctgggcaactagaatgcagtgaaaaaaatgctttatttgtgaaatttgtgatgctatt gctttatttgtaaccattataagctgcaataaacaagttaacaacaac |
| 26 | U1_theo_9 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtataccagccgaaaggcccttggcagacttac ctgggcaactagaatgcagtgaaaaaaatgctttatttgtgaaatttgtgatgctattgc tttatttgtaaccattataagctgcaataaacaagttaacaacaac |
| 27 | U1_theo_8_1 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagcactt acctggacaactagaatgcagtgaaaaaaatgctttatttgtgaaatttgtgatgctatt gctttatttgtaaccattataagctgcaataaacaagttaacaacaac |
| 28 | U1_theo_8_2 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagcactt acctgaacaactagaatgcagtgaaaaaaatgctttatttgtgaaatttgtgatgctatt gctttatttgtaaccattataagctgcaataaacaagttaacaacaac |
| 29 | U1_theo_8_3 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcactt acctaaacaactagaatgcagtgaaaaaaatgctttatttgtgaaatttgtgatgctatt gctttatttgtaaccattataagctgcaataaacaagttaacaacaac |
| 30 | U1_theo_8_4 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagcactt accaaaacaactagaatgcagtgaaaaaaatgctttatttgtgaaatttgtgatgctatt gctttatttgtaaccattataagctgcaataaacaagttaacaacaac |
| 31 | U1_theo_8_5 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtggataccagccgaaaggcccttggcagcactt acaaaaacaactagaatgcagtgaaaaaaatgctttatttgtgaaatttgtgatgctatt gctttatttgtaaccattataagctgcaataaacaagttaacaacaac |
| 32 | U1_theo_8_6 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagcactt aaaaaaacaactagaatgcagtgaaaaaaatgctttatttgtgaaatttgtgatgctatt gctttatttgtaaccattataagctgcaataaacaagttaacaacaac |
| 33 | U1_theo_8_7 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagcactt caaaaaacaactagaatgcagtgaaaaaaatgctttatttgtgaaatttgtgatgctatt gctttatttgtaaccattataagctgcaataaacaagttaacaacaac |
| 34 | U1_theo_8_8 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagacta caaaaaacaactagaatgcagtgaaaaaaatgctttatttgtgaaatttgtgatgctatt gctttatttgtaaccattataagctgcaataaacaagttaacaacaac |
| 35 | U1_theo_8_9 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagaca acaaaaaacaactagaatgcagtgaaaaaaatgctttatttgtgaaatttgtgatgctat tgctttatttgtaaccattataagctgcaataaacaagttaacaacaac |
| 36 | U1_theo_9_1 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagacttac |

| SEQ ID NO.: | Description | Sequence |
|---|---|---|
| | | ctggacaactagaatgcagtgaaaaaaatgctttatttgtgaaatttgtgatgctattgct ttatttgtaaccattataagctgcaataaacaagttaacaacaac |
| 37 | U1_theo_9_2 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtataccagccgaaaggcccttggcagacttac ctgaacaactagaatgcagtgaaaaaaatgctttatttgtgaaatttgtgatgctattgct ttatttgtaaccattataagctgcaataaacaagttaacaacaac |
| 38 | U1_theo_9_3 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtataccagccgaaaggcccttggcagacttac ctaaacaactagaatgcagtgaaaaaaatgctttatttgtgaaatttgtgatgctattgct ttatttgtaaccattataagctgcaataaacaagttaacaacaac |
| 39 | U1_theo_9_4 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtataccagccgaaaggcccttggcagacttac caaaacaactagaatgcagtgaaaaaaatgctttatttgtgaaatttgtgatgctattgc tttatttgtaaccattataagctgcaataaacaagttaacaacaac |
| 40 | U1_theo_9_5 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtataccagccgaaaggcccttggcaacttac aaaaacaactagaatgcagtgaaaaaaatgctttatttgtgaaatttgtgatgctattgc tttatttgtaaccattataagctgcaataaacaagttaacaacaac |
| 41 | U1_theo_9_6 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtataccagccgaaaggcccttggcagacttaa aaaaacaactagaatgcagtgaaaaaaatgctttatttgtgaaatttgtgatgctattgc tttatttgtaaccattataagctgcaataaacaagttaacaacaac |
| 42 | U1_theo_9_7 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtataccagccgaaaggcccttggcagacttca aaaaacaactagaatgcagtgaaaaaaatgctttatttgtgaaatttgtgatgctattgc tttatttgtaaccattataagctgcaataaacaagttaacaacaac |
| 43 | U1_theo_9_8 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtataccagccgaaaggcccttggcagactaca aaaaacaactagaatgcagtgaaaaaaatgctttatttgtgaaatttgtgatgctattgc tttatttgtaaccattataagctgcaataaacaagttaacaacaac |
| 44 | 4xU1_theo_8_1 in pRL-SV40 | TCAAATCGTTCGTTGAGCGAGTTCTCAAAAATGAA CAATAAttctagagcggccgcttcgagcagacatgataagatacattgatgagt ttggacaaaccaaacccaggtaagtgataccagccgaaaggcccttggcagcactt acctggacaactagaatgcagtgaaaaaagagtttggacaaaccaaacccaggtaa gtgataccagccgaaaggcccttggcagcacttacctggacaactagaatgcagtg aaaaaaatgcgagtttggacaaaccaaacccaggtaagtgataccagccgaaaggcccttggcagc acttacctggacaactagaatgcagtgaaaaaaatgctttatttgtga gagtttggacaaaccaaacccaggtaagtgataccagccgaaaggcccttggcag cacttacctggacaactagaatgcagtgaaaaaaatgctttatttgtgaaatttgtgatg ctattgctttatttgtaaccattataagctgcaataaacaagttaacaacaac |
| 45 | U1_Gua_1 wt in pFLuc | TCATAAAGGCCAAGAAGGGCGGAAAGATCGCCGT GTAAgccataccacattaaggtaatgtataatcgcgtggatatggcacgcaagttt ctaccgggcaccgtaaatgtccgactacattactgtagaggttttacttgctttaaaaaa cctcccacacctcccctgaacctgaaacataaaatgaatgcaattgttgttgttaactt gtttattgcagcttataatggttacaaataaagcaatagcatcacaaatttcacaaataaa gcattttttcactgcattctagttgtggtttgtccaaactcatcaatgtatcttaa |
| 46 | U1_Gua_1 mut in pFLuc | TCATAAAGGCCAAGAAGGGCGGAAAGATCGCCGT GTAAgccataccacattaatggaatctataatcgcgtggatatggcacgcaagttt ctaccgggcaccgtaaatgtccgactagattcctgtagaggttttacttgctttaaaaaa cctcccacacctcccctgaacctgaaacataaaatgaatgcaattgttgttgttaactt gtttattgcagcttataatggttacaaataaagcaatagcatcacaaatttcacaaataaa gcattttttcactgcattctagttgtggtttgtccaaactcatcaatgtatcttaa |
| 47 | U1_Gua_2 wt in pFLuc | TCATAAAGGCCAAGAAGGGCGGAAAGATCGCCGT GTAAgccataccacatttgtagaggttttacttgctttaaaaaacctcccacaccta aggtaatgtataatcgcgtggatatggcacgcaagtttctaccgggcaccgtaaatgt ccgactacattaccccctgaacctgaaacataaaatgaatgcaattgttgttgttaact tgtttattgcagcttataatggttacaaataaagcaatagcatcacaaatttcacaaataaa gcattttttcactgcattctagttgtggtttgtccaaactcatcaatgtatcttaa |

-continued

| SEQ ID NO.: | Description | Sequence |
|---|---|---|
| 48 | U1_Gua_2 mut in pFLuc | TCATAAAGGCCAAGAAGGGCGGAAAGATCGCCGT<br>GTAAgccataccacatttgtagaggttttacttgctttaaaaaacctcccacaccta<br>atggaatctataatcgcgtggatatggcacgcaagtttctaccgggcaccgtaaatgt<br>ccgactagattccccccctgaacctgaaacataaaatgaatgcaattgttgttgttaact<br>tgtttattgcagcttataatggttacaaataaagcaatagcatcacaaatttcacaaataaa<br>gcattttttcactgcattctagttgtggtttgtccaaactcatcaatgtatcttaa |
| 49 | U1_Gua_3 wt in pFLuc | TCATAAAGGCCAAGAAGGGCGGAAAGATCGCCGT<br>GTAAgccataccacatttgtagaggttttacttgctttaaaaaacctcccacaccctc<br>cccctgaacctgaaacataaaatgaatgcaattgtaaggtaatgtataatcgcgtgga<br>tatggcacgcaagtttctaccgggcaccgtaaatgtccgactacattactgttgttaact<br>tgtttattgcagcttataatggttacaaataaagcaatagcatcacaaatttcacaaataaa<br>gcattttttcactgcattctagttgtggtttgtccaaactcatcaatgtatcttaa |
| 50 | U1_Gua_3 mut in pFLuc | TCATAAAGGCCAAGAAGGGCGGAAAGATCGCCGT<br>GTAAgccataccacatttgtagaggttttacttgctttaaaaaacctcccacaccctc<br>cccctgaacctgaaacataaaatgaatgcaattgtaatggaatctataatcgcgtggat<br>atggcacgcaagtttctaccgggcaccgtaaatgtccgactagattcctgttgttaact<br>tgtttattgcagcttataatggttacaaataaagcaatagcatcacaaatttcacaaataaa<br>gcattttttcactgcattctagttgtggtttgtccaaactcatcaatgtatcttaa |
| 51 | wtU1_Gua_HBGPA | TCATAAAGGCCAAGAAGGGCGGAAAGATCGCCGT<br>GTAAggatccaagcttatcgataccgtcgacctcgaggtaatgtataatcgcgtg<br>gatatggcacgcaagtttctaccgggcaccgtaaatgtccgactacattacggccca<br>gatctaattcaccccaccagtgcaggctgcctatcagaaagtggtggctggtgtggc<br>taatgccctggcccacaagtatcactaagctcgctttcttgctgtccaatttctattaaag<br>gttcctttgttccctaagtccaactactaaactgggggatattatgaagggccttgagc<br>atctggattctgcctaataaaaacatttattttcattgcaatgatgtattt |
| 52 | mutU1_Gua_HBGPA | TCATAAAGGCCAAGAAGGGCGGAAAGATCGCCGT<br>GTAAggatccaagcttatcgataccgtcgacctcgatggaatctataatcgcgtg<br>gatatggcacgcaagtttctaccgggcaccgtaaatgtccgactacattacggccca<br>gatctaattcaccccaccagtgcaggctgcctatcagaaagtggtggctggtgtggc<br>taatgccctggcccacaagtatcactaagctcgctttcttgctgtccaatttctattaaag<br>gttcctttgttccctaagtccaactactaaactgggggatattatgaagggccttgagc<br>atctggattctgcctaataaaaacatttattttcattgcaatgatgtattt |

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. All references cited herein are hereby incorporated by reference in their entirety.

EXAMPLE 1

Effects on target gene expression of location and copy number of U1 binding site in 3' UTR Experimental procedure:

Plasmid constructs: oligonucleotides (oligos) containing either wild type consensus U1 binding sequence or its mutant sequence were synthesized (IDT). The synthesized oligos were cloned into the 3' UTR of the pRL-SV40 luciferase expression vector (Promega) using Gibson Assembly Cloning Kit (NEB). Constructs were purified (Qiagen) and verified by DNA sequencing (Genewiz).

Transfection: $3.5 \times 10^4$ HEK 293 cells were plated in a 96-well flat bottom plate the day before transfection. Plasmid DNA (500 ng) was added to a tube or a 96-well U-bottom plate. Separately, TransIT-293 reagent (Mirus; 1.4 µl) was added to 50 µl Opti-mem I media (Life Technologies), and allowed to sit for 5 minutes at room temperature ("RT"). Then, 50 µl of this diluted transfection reagent was added to the DNA, mixed, and incubated at RT for 20 min. Finally, 7 µl of this solution was added to a well of cells in the 96-well plate.

Renilla luciferase assay of cultured cells: 24 hours after the media change, plates were removed from the incubator, and equilibrated to RT for several minutes on a lab bench, and the media aspirated. Glo-lysis buffer (Promega, 100 µl, RT) was added, and the plates allowed to remain at room temp for at least 5 minutes. Then, the well contents were mixed by 50 µl trituration, and 20 µl of each well was mixed with 20 µl of Renilla-glo reagent in a solid-white 384-well plate. Ten minutes later, luminescence was measured using a Tecan machine with 500 msec read time. The luciferase activity was expressed as mean relative light unit (RLU) ±SD.

Figure 1A:
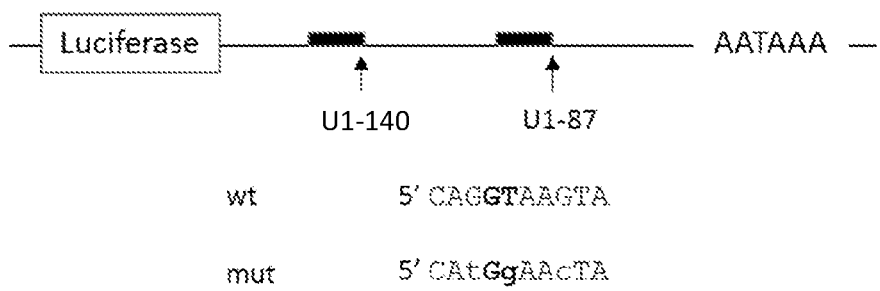
FIGS. 1*a*-1*b*. U1 binding site in 3' UTR suppresses target gene (luciferase) expression.
Figure 1B:
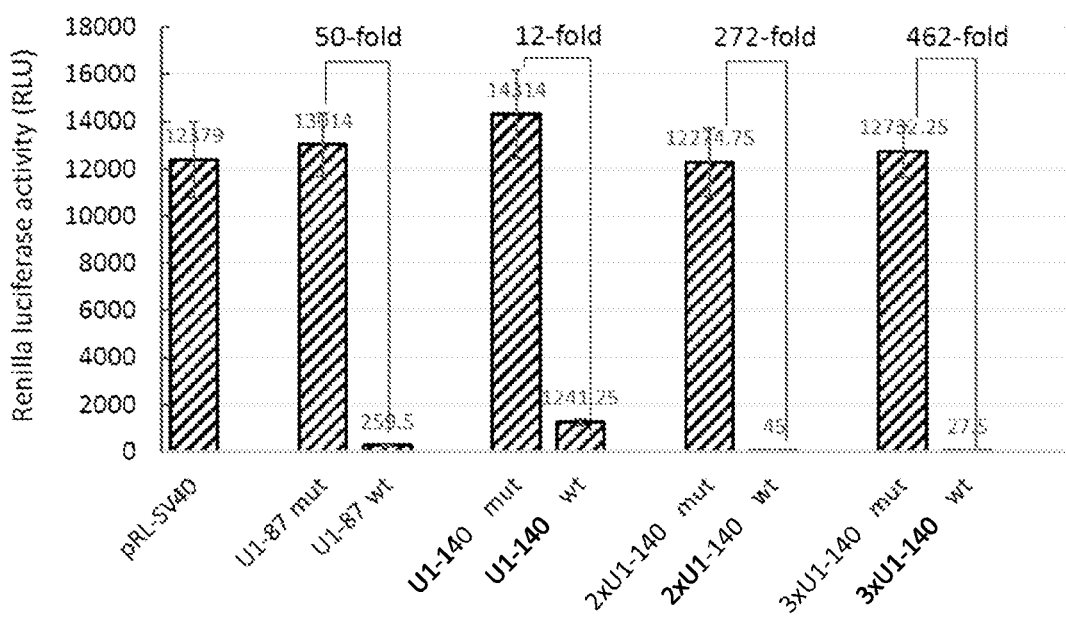

Results:

In order to build a U1-polyadenylation-based gene regulation platform, a U1 binding sequence was inserted into the 3' UTR of a target reporter gene. The 10 nucleotide ("nt") consensus U1 binding sequence (referred to herein as wild-type or wt) was placed either 87 nt (U1-87) or 140 nt (U1-140) upstream of the AATAAA poly(A) sequence in the 3' UTR in of the luciferase gene in the pRL-SV40 vector, as shown in FIG. 1a. As shown in FIG. 1b, insertion of 10-nt mutant U1 binding sequence at −87 position (U1-87 mut) did not have any suppressive effect on luciferase gene expression compared to expression from the unmodified pRL-SV40 construct. However, insertion of a 10-nt wild type U1 binding sequence at the −87 position (U1-87 wt) inhibited 98% of Renilla luciferase expression when compared to luciferase activity from the pRL-SV40 control vector. When compared with the U1-87 mut construct, the U1-87 wt generated 50-fold decrease in luciferase activity.

Similarly, the mutant U1 site at—140 (U1-140 mut) did not cause inhibition of luciferase gene expression. However, the wild type U1 binding sequence at the—140 location (U1-140 wt) resulted in 91% inhibition of luciferase activity, generating 12-fold inhibition of luciferase activity when compared to the U1-140 mut.

The inhibitory effect of either 2 copies or 3 copies of U1 binding sequence inserted at −140 in 3' UTR was also tested. As shown in FIG. 1b, 2 copies (2×U1-140 wt) or 3 copies (3×U1-140 wt) of the wild type U1 binding sequence resulted in further reduction in luciferase activity when compared to single copy of U1 site at the same location (U1-140 wt), generating 272-fold and 462-fold inhibition, respectively, when compared to their corresponding mutant constructs. Thus, these results indicate that multiple copies of U1 binding sequence have synergistic function in suppressing gene expression.

EXAMPLE 2

Figures 2A, 2B:
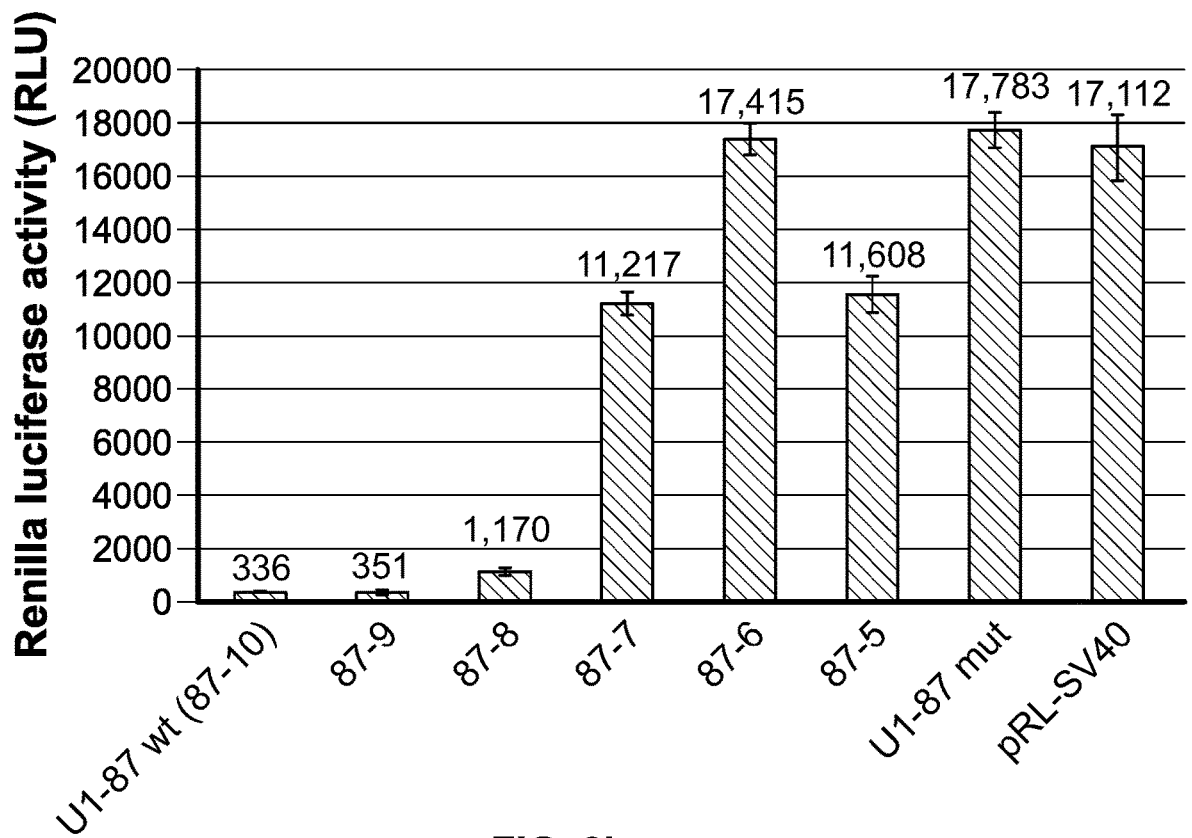
FIGS. 2a-2b. Effect of the length of the U1 binding sequence in the 3' UTR on suppression of gene expression.

Effect on target gene expression of the length of U1 binding sequence in the 3' UTR.
Experimental procedures: as described in Example 1.
Results:
Based on the results described in Example 1, the suppressive effect of a U1 binding site inserted 87 nt (U1-87) upstream of the SV40 late polyA signal sequence was further characterized. In order to determine the minimal length of the U1 binding sequence for repressing target gene expression when placed in the 3', a series of constructs containing 3' sequentially-truncated sequence of U1 site, as shown in FIG. 2a. As shown in FIG. 2b, 9-nt U1 site (87-9) functioned as well as the 10-nt U1 site (U1-87). However, when the U1 binding sequence was truncated to 8 nt, the suppressive effect of the U1 site was somewhat reduced, resulting in 3-fold less efficiency. When the U1 site sequence was 7 nt or shorter, the suppressive effect was significantly less efficient. These results indicate that U1 binding site inserted 87 nt upstream of SV40 late poly(A) signal in 3' UTR is more effective at repressing target gene expression when at least 8 nt long in order to recruit U1 snRNP efficiently to suppress polyadenylation. A 9 nt U1 binding sequence inserted 87 nt upstream of SV40 late polyA signal sequence was selected for further characterization.

EXAMPLE 3

Figure 3A:
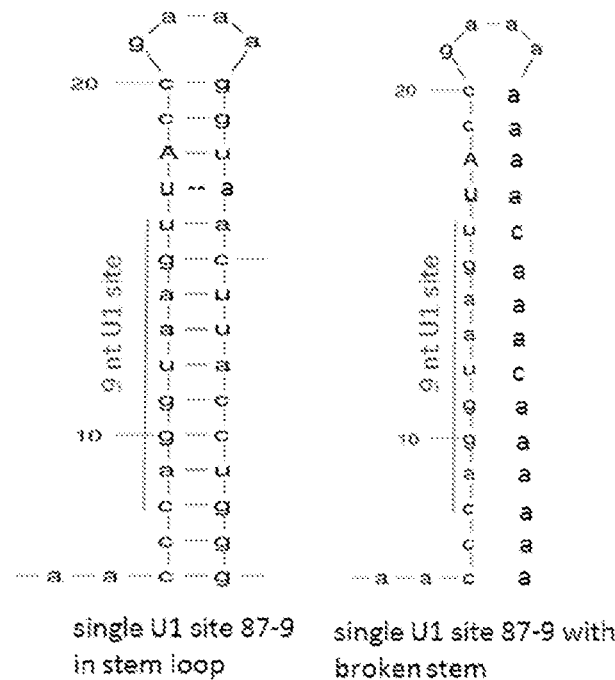
FIGS. 3a-3b. The effect of stem-loop structure at the U1 site in 3' UTR on gene expression.
Figure 3B:
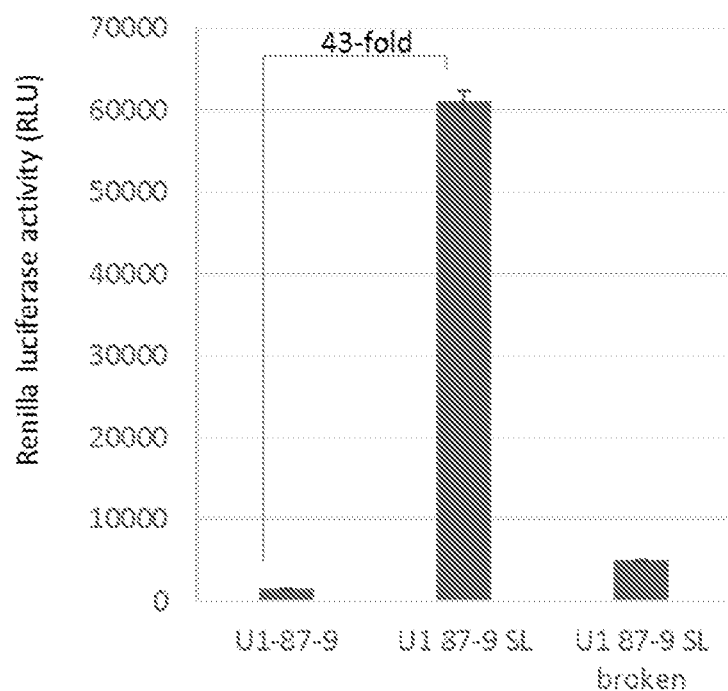

The effect of stem-loop secondary structure formation at the U1 site in 3' UTR on gene expression
Experimental Procedure:
The stem-loop sequences containing a wild type 9 nt U1 binding sequence were synthesized (IDT) and cloned into pRL-SV40 vector. The construct sequences were verified by DNA sequencing (Genewiz). HEK 293 cells were transfected and Renilla luciferase assay were performed as described in Example 1.
Results:
To determine the effect of a hairpin or stem-loop structure on the U1 site-mediated suppression of gene expression, the 9 nt U1 site was embedded in a stem-loop (SL) structure. In this stem-loop structure, as shown in FIG. 3a, the U1 site and its complementary sequence forms the stem. A mutant sequence was made as control in which no stem is formed (SL broken). As shown in FIG. 3b, embedding the 9 nt U1 site in the stem-loop structure (U1 87-9 SL) completely abolished the suppressive effect of the U1 site in the 3' UTR, whereas the control sequence that can't form stem-loop structure (U1 87-9 SL broken) showed little effect on the suppressive function of U1 site. These results support that a U1 site embedded in stem-loop structure is not accessible to U1 snRNP binding, therefore gene expression is not suppressed by U1 snRNP-mediated suppression of polyadenylation.

EXAMPLE 4

Figure 4A:
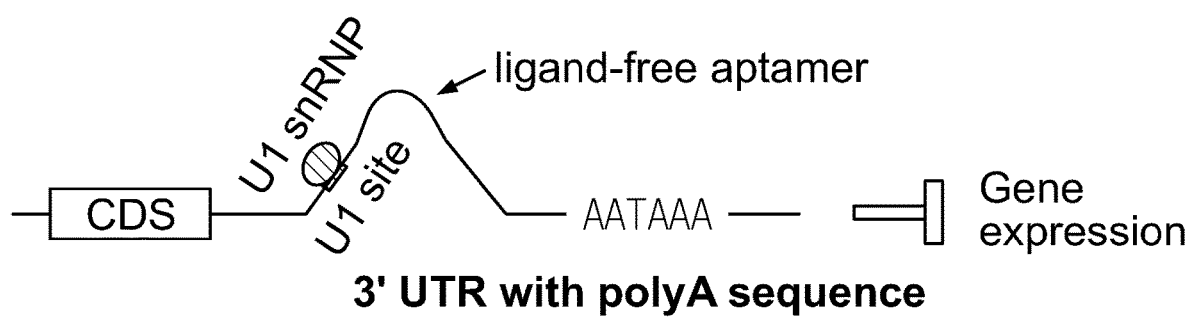
FIGS. 4a-4c. Use of a theophylline aptamer to regulate U1 interference in 3' UTR of a target gene.
Figure 4A:
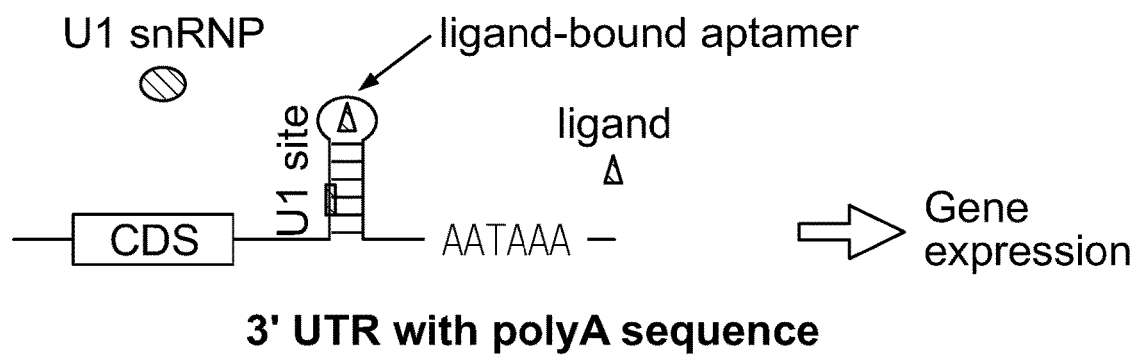

Use of theophylline aptamer to regulate target gene expression via modulating U1 interference with polyadenylation
Experimental procedures:
Oligonucleotides containing either the full length of sequences of the stem from the stem-loop structure and theophylline aptamer or the truncated sequences of the stem, were synthesized (IDT) and cloned into pRL-SV40 vector using the Gibson Assembly Cloning Kit (NEB). Construct sequences were verified by DNA sequencing (Genewiz).
Transfection and aptamer ligand treatment: HEK 293 cells were transfected as described in Example 1. Four hours after transfection, the media was aspirated, and new media with or without 3 mM theophylline was added. A Renilla luciferase assay was performed 20 to 24 hours after theophylline treatment as described in Example 1. The induction fold was expressed as the quotient of luciferase activity obtained in the presence of aptamer ligand divided by the value obtained in the absence of the aptamer ligand.
Results:
In order to regulate the accessibility of a U1 site in the 3' UTR of a target gene, and thereby regulate target gene expression, the stem sequence of the aptamer structure was linked directly to the stem of the stem-loop structure tested in Example 3. In this configuration, as illustrated in FIG. 4a, insertion of aptamer sequence disrupts the formation of the stem structure, therefore, the U1 site in the 3' UTR is accessible to U1 snRNP binding. However, in the presence of aptamer ligand, aptamer/ligand binding causes a RNA structure conformational change, facilitating stem formation and sequestering U1 site from U1 snRNP binding in 3' UTR.

Figure 4B:
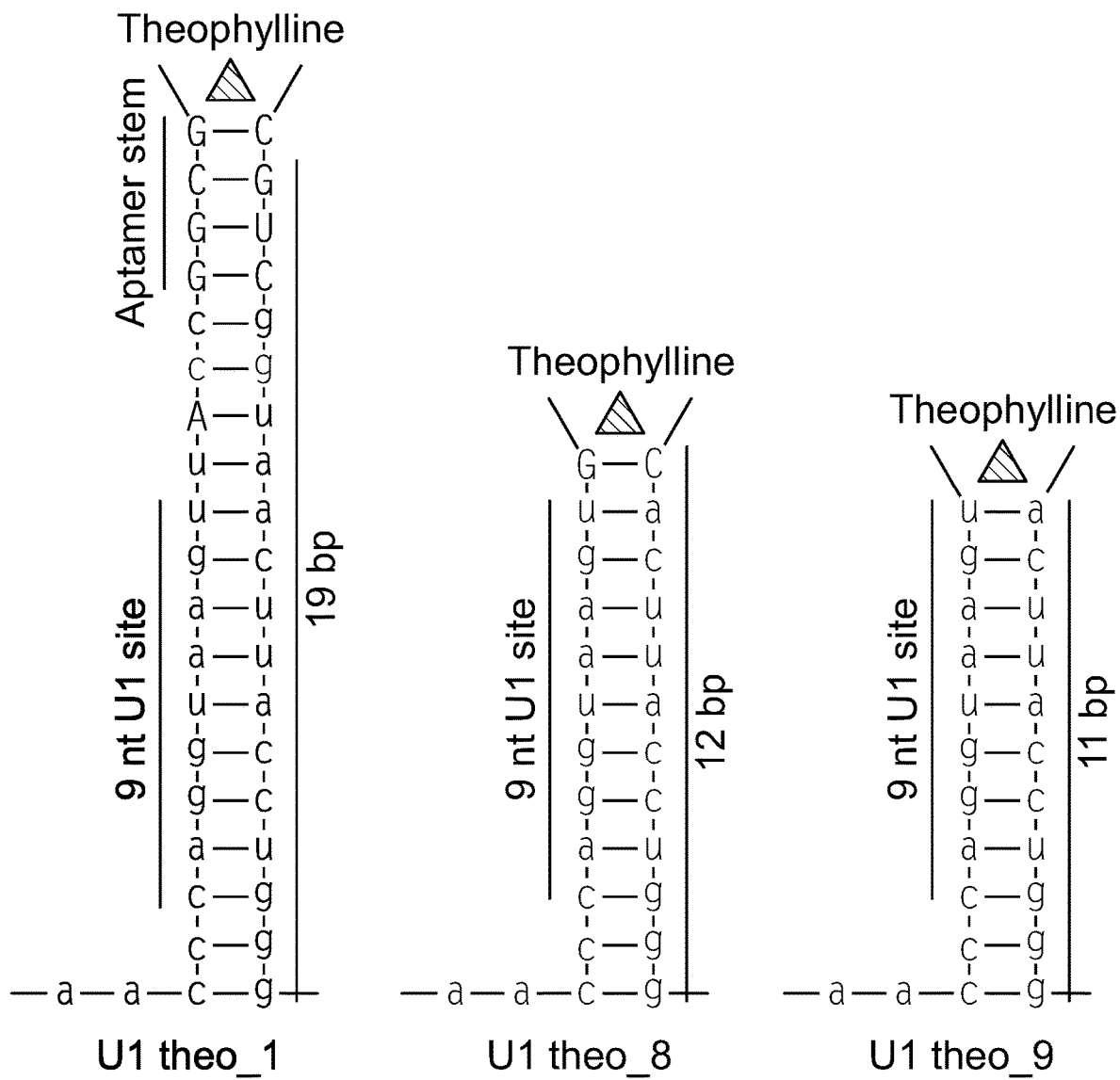
Figure 4C:
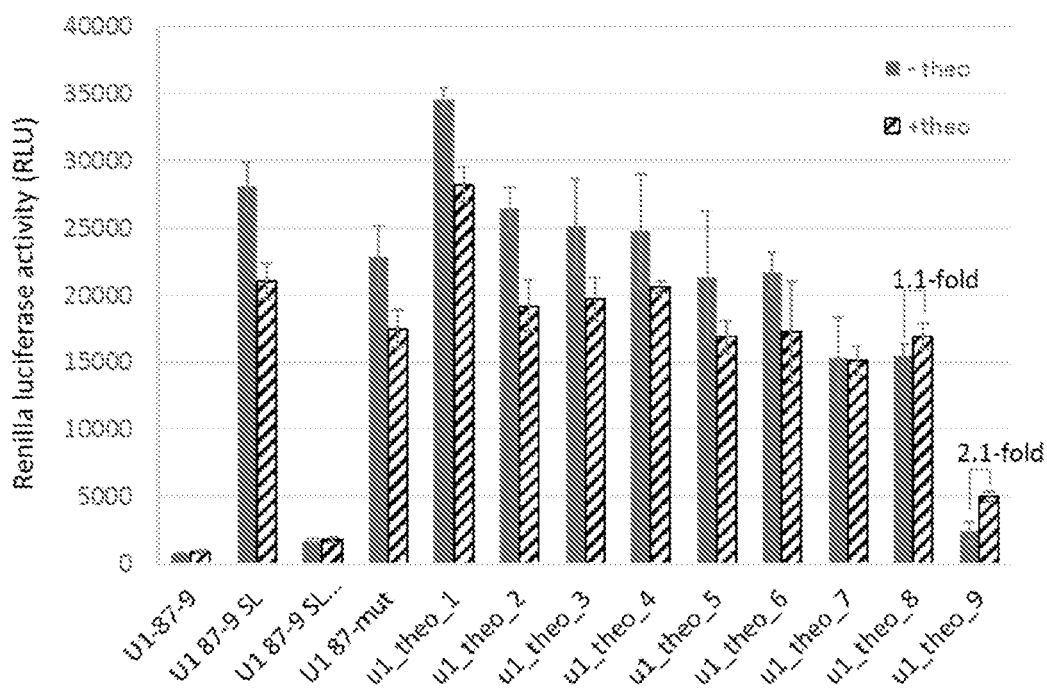

A synthetic theophylline aptamer was tested in this configuration by linking the lower stem sequence of the theophylline aptamer structure to the stem of the stem-loop structure, which generated a 19 base pair stem as shown in FIG. 4b. We rationalized that if the stem is too long, the stem formation could be independent of the existence of aptamer sequence and occur in the absence of aptamer ligand. Conversely, if the stem is too short, even in the presence of aptamer ligand, a stable aptamer structure cannot be achieved. Therefore, to determine an optimal length of the stem (including any stem from the aptamer and the stem containing U1 binding site), serial truncations to the stem were made, generating 9 constructs with the length of the stem ranging from 19 to 11 bp. As shown in FIG. 4c, with constructs U1_theo_1 through U1_theo_6, the luciferase activity was not suppressed significantly comparing to construct U1 87-9 in the absence of theophylline, suggesting the sequestering of the U1 site due to stem formation. Further, there was no increase in the luciferase activity after theophylline treatment. However, in construct 8 and 9, the luciferase activity was increased after theophylline treatment, suggesting aptamer/ligand binding further blocks U1 site accessibility, leading to increased target gene expression.

EXAMPLE 5

Optimization of the stem sequence to enhance the regulatability of U1 accessibility due to aptamer/ligand binding Experimental procedures: As described in Example 4.

Figure 5A:
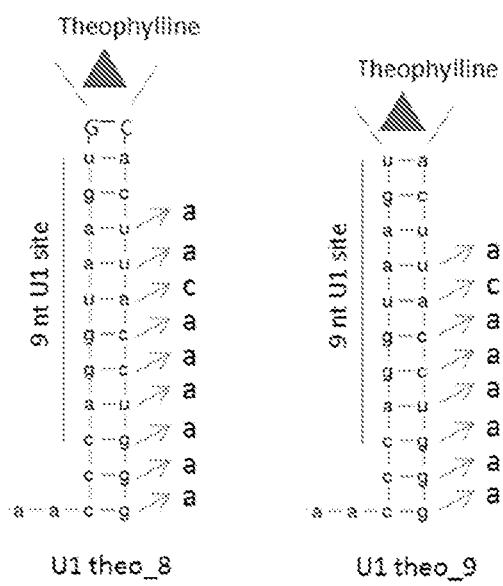
FIGS. 5a-5c. Optimization of effector region stem sequence to enhance the regulatability of U1 site accessibility.
Figure 5B:
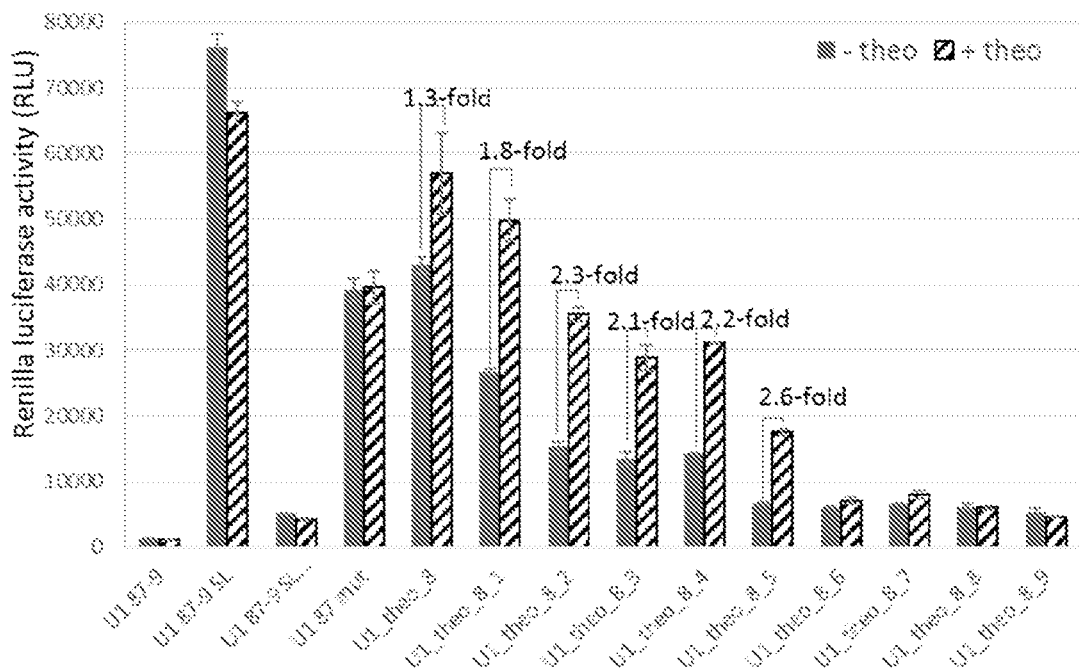
Figure 5C:
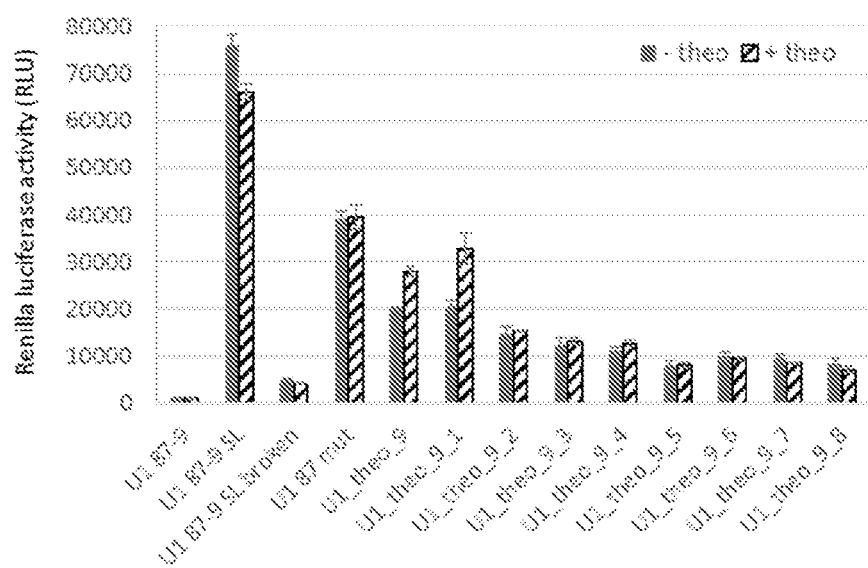

Results:

Constructs U1_theo_8 and 9 showed small increase in luciferase activity after theophylline treatment. To further enhance the regulatability of the U1 site accessibility when the aptamer is not bound by ligand, the stem structure was weakened by sequentially mutating the stem bases, as shown in FIG. 5a. Though, this strategy did not improve the induction of luciferase activity from construct U1_theo_9, as shown in FIG. 5c, it improved regulatability of construct U1_theo_8. As shown in FIG. 5b, in a series of 9 constructs made from U1_theo_8, constructs U1_theo_8_1 through 5 generated increased luciferase activity after theophylline treatment when compared to luciferase activity in the absence of aptamer ligand. The induction fold was increased when comparing with the induction fold of U1_theo_8 construct (1.3 fold), ranging from 1.8 to 2.6 fold. Therefore, we have built a synthetic riboswitch that regulates U1 interference with polyadenylation through aptamer/ligand binding.

EXAMPLE 6

Effects of multiple U1_theo riboswitch on regulating target gene expression

Experimental procedures:

Oligos containing 4 copies of the U1_theo_8_1 sequence in tandem were synthesized (IDT) and cloned using Gibson strategy and cloning kit (NEB). HEK 293 cells were transfected and Renilla luciferase assay was performed as described in Example 4.

Figure 6A:
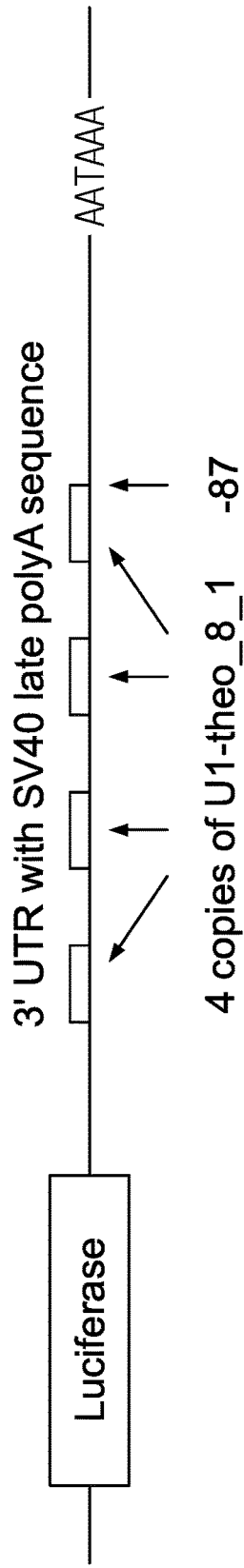
FIGS. 6a-6b. Effect of multiple U1_theo riboswitches in the 3' UTR on regulation of target gene expression.
Figure 6B:
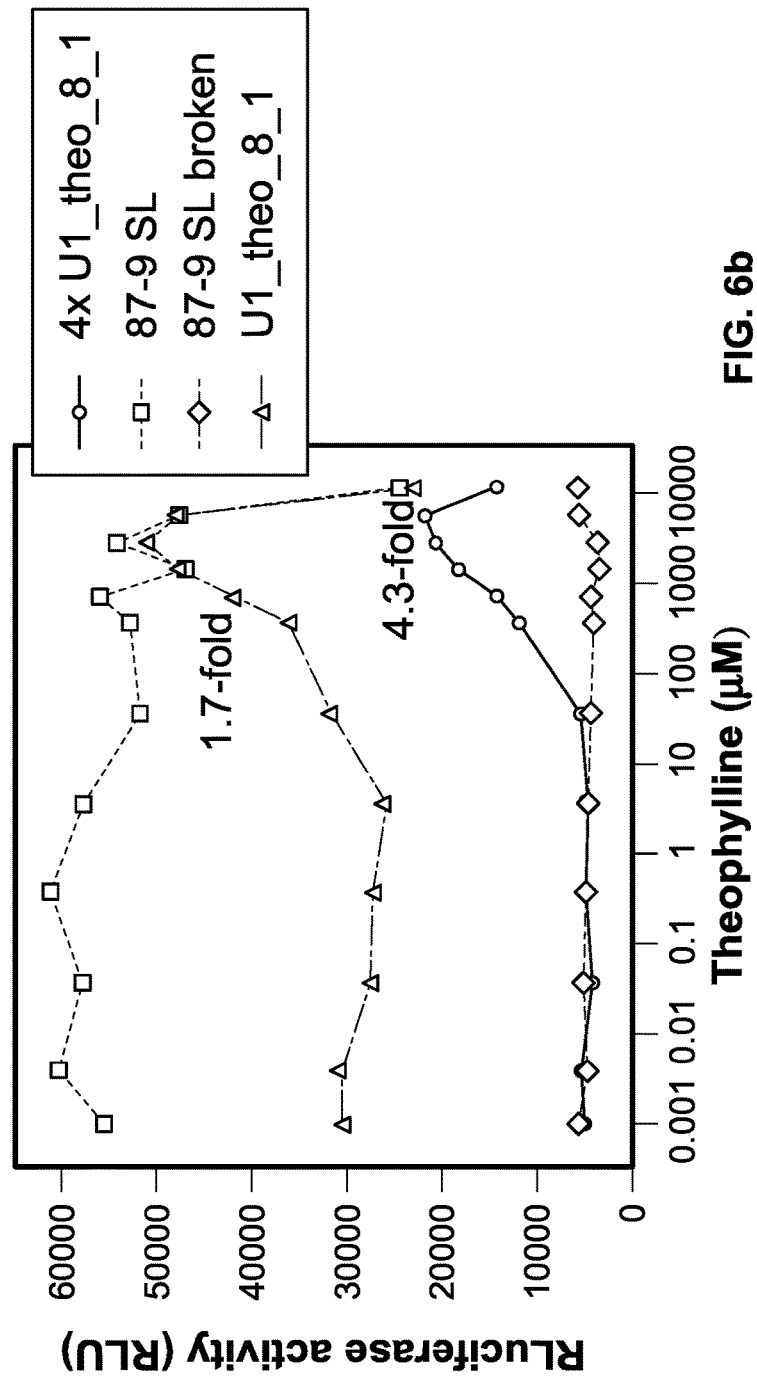

Results:

Construct U1_theo_8-1 generated 1.8-fold induction after theophylline treatment, due to relatively high basal level expression of luciferase gene. In order to lower the basal level expression of the target gene, 4 copies of the U1_theo_8_1 sequence was placed in tandem in the 3' UTR, as shown in FIG. 6a. Indeed, as shown in FIG. 6b, 4 copies of U1-theo_8_1 did reduce the basal level expression by 83% comparing to the single copy of U1_theo_8_1. Upon theophylline treatment, the 4-copy construct increased the luciferase activity in a dose-dependent manner, generating 40% of the luciferase activity of 87-9 SL control vector and maximal 4.3-fold induction at 6 mM theophylline. These results indicate that multiple copies of the U1 site riboswitch in tandem can reduce basal expression level of the target gene, improving target gene regulatability. In the current construct configuration, the same aptamer sequence was used in all 4 copies of regulation cassettes. Different aptamer sequences can be used in each copy of the riboswitch.

EXAMPLE 7

Use of xpt-guanine aptamer to regulate target gene expression via modulating U1 interference Experimental procedures:

Plasmid constructs: The EGFP gene in pEGFP-C1 vector was replaced with firefly luciferase gene coding sequence to generate a pFLuc vector that contains an SV40 early polyadenylation signal sequence. Oligos containing either wild type or mutant U1 binding site from the 5' splice site of human DHFR exon 2 and xpt-guanine aptamer sequence followed by the complementary sequence of the last 7 nt of the U1 site sequence were synthesized (IDT) and cloned into the pFLuc vector using the Gibson cloning strategy and kit (NEB).

Transfection and aptamer ligand treatment: HEK 293 cells were transfected as described in Example 1. Four hours after transfection, the media was aspirated, and new media with or without 500 μM guanine was added.

Firefly luciferase assay of cultured cells: Twenty-four hours after the media change, the plates were removed from the incubator, and equilibrated to RT for several minutes on a lab bench, then aspirated. Glo-lysis buffer (Promega, 100 uL, RT) was added, and the plates allowed to remain at RT for at least 5 minutes. Then, the well contents were mixed by 50 uL trituration, and 20 uL of each sample was mixed with 20 μL of bright-glo reagent (Promega) that had been diluted to 10% in glo-lysis buffer. The 96 wells were spaced on an opaque white 384-well plate. Following a 5 min incubation at RT, luminescence was measured using a Tecan machine with 500 mSec read time. The luciferase activity was expressed as mean relative light unit (RLU)±S.D.

Figure 7A:
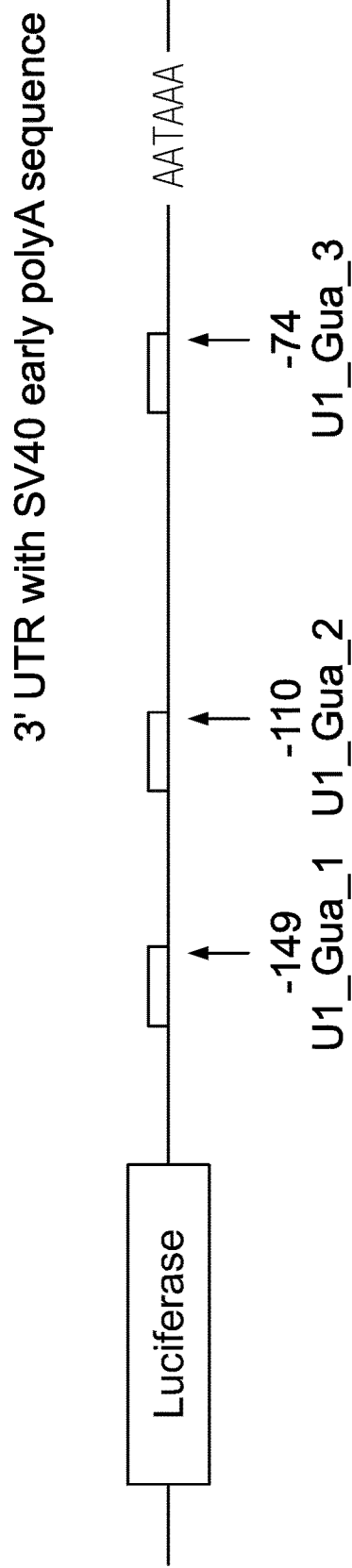
FIGS. 7a-7c. Use of guanine aptamer to modulate U1 interference.
Figure 7B:
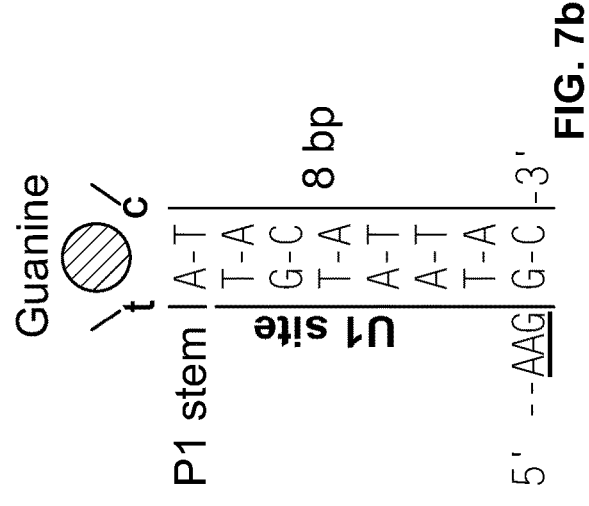
Figure 7C:
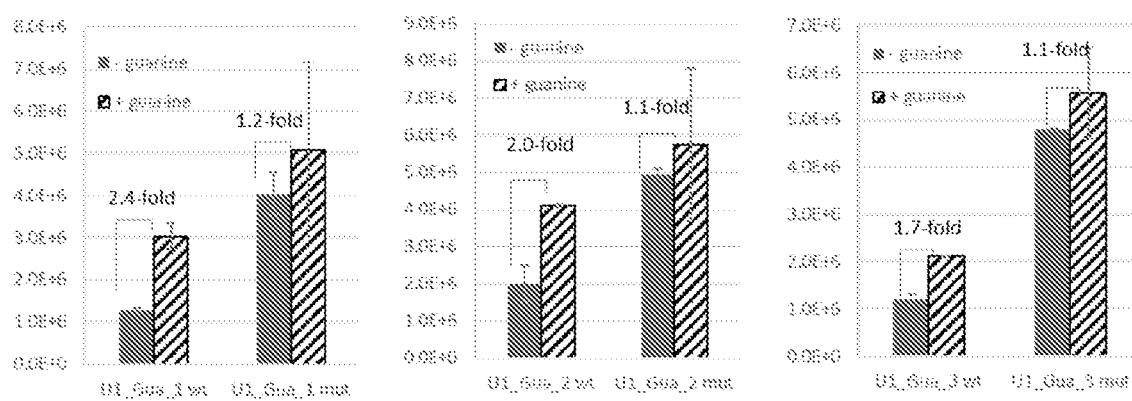

Results:

The use of additional aptamer/ligand pair, either synthetic or natural aptamers, in this U1-interference based, gene regulation platform was tested by inserting a 10 nt U1 site, the 5' splice site from DHFR exon 2, linked with xpt-guanine aptamer at different positions in pRLuc vector, as shown in FIG. 7a. In this 10 nt U1 site, only the last 7 nt were designed to base pair with its complementary sequence located at the 3' end of xpt-guanine aptamer sequence, as shown in FIG. 7b. This sequence configuration was generated through a serial truncation of the stem sequence connecting the aptamer P1 stem and stem formed by the U1 site and its complementary sequence, and demonstrated high dynamic range in alternative splicing based aptamer riboswitch. In this study, we placed this sequence configuration at either 149 nt, 110 nt or 74 nt upstream of the SV40 early poly(A) signal sequence in 3' UTR region, generating U1_Guan_1, 2 and 3 constructs. In addition, a mutant U1 site was generated as a control sequence. As shown in FIG. 7c, upon guanine treatment, the luciferase activity increased 2.4, 2.0 and 1.7 fold from U1_Gua_1, 2, and 3 constructs, respectively.

EXAMPLE 8

Aptamer-modulated U1 interference is not polyA sequence specific

Experimental procedures:

Plasmid constructs: SV40 early polyadenylation sequence was replaced with human beta globin polyA sequence in pFLuc vector to generate pFLuc_HBGPA. Oligos containing either wild type or mutant U1 binding site from 5' ss of human DHFR exon 2 and xpt-guanine aptamer sequence followed by the complementary sequence of last 7 nt of U1 site sequence were synthesized (IDT) and cloned into pFLuc_HBGPA vector using Gibson cloning strategy and kit (NEB).

Transfection and luciferase assay were as described in Example 7.

Results:

We have demonstrated aptamer-modulated U1 interference with polyadenylation in the context of either SV40 late polyA sequence or SV40 early polyA sequence, as shown in Example 4-6. Further, to demonstrate the aptamer-modulated U1 interference, thus target gene expression was not limited to SV40 polyA sequences, we tested the guanine aptamer-modulated U1 interference in the context of the polyA sequence from human beta globin gene. As shown in FIG. 8, upon guanine treatment, the luciferase activity increased 2.1 fold from wtU1_Gua_HBGPA construct. In contrast, the mutU1_Gua_HBGPA didn't induce luciferase activity when comparing to the untreated samples. These results demonstrate that aptamer-modulated U1 interference is not polyA sequence specific.

We claims:

1. A polynucleotide construct for the regulation of the expression of a target gene comprising a polynucleotide sequence comprising the target gene coding sequence and a 3' untranslated region (UTR) comprising a polyadenylation signal, and a riboswitch, wherein the riboswitch comprises an effector region and an aptamer, wherein the effector region comprises a stem-forming sequence that is 8 to 11 base pairs comprising a U1 snRNP binding site and sequence complementary to the U1 snRNP binding site, wherein the riboswitch is located in the 3' UTR of the target gene 5' of the polyadenylation signal.

2. The polynucleotide construct of claim 1, wherein the aptamer binds a small molecule ligand.

3. The polynucleotide construct of claim 1, wherein the effector sequence comprises additional sequence that is capable of forming a stem when the aptamer binds ligand.

4. The polynucleotide construct of claim 3, wherein the effector region comprises a stem-forming sequence that is 9 to 11 base pairs.

5. The polynucleotide construct of claim 4, wherein the effector region comprises a stem-forming sequence with one or more mismatched bases in the stem.

6. The polynucleotide construct of claim 1, wherein the U1 snRNP binding site is 8 to 10 nucleotides.

7. The polynucleotide construct of claim 1, wherein the U1 snRNP binding site comprises the sequence CAGGTAAG (SEQ ID NO: 53).

8. The polynucleotide construct of claim 1, wherein the U1 snRNP binding site is selected from the group consisting of CAGGTAAGTA (SEQ ID NO: 1), CAGGTAAGT (SEQ ID NO: 54), and CAGGTAAG (SEQ ID NO: 53).

9. A polynucleotide construct of claim 1, wherein the polynucleotide construct comprises two or more riboswitches located in the 3' UTR of the target gene, wherein each riboswitch comprises an effector region and an aptamer, wherein the effector region comprises a U1 snRNP binding site and sequence complementary to the U1 snRNP binding site.

10. The polynucleotide construct of claim 9, wherein the two or more riboswitches each comprise an aptamer that binds the same ligand.

11. The polynucleotide construct of claim 9, wherein the two or more riboswitches comprise different aptamers that bind different ligands.

12. A method of modulating the expression of a target gene comprising:
   a. introducing the polynucleotide construct of claim 1 into a cell, and
   b. exposing the cell to a ligand that specifically binds the aptamer in an amount effective to increase expression of the target gene.

13. The method of claim 12, wherein the ligand is a small molecule.

14. The method of claim 12, wherein the riboswitch is inserted about 87 or about 140 nucleotides 5' of the polyadenylation signal.

15. The method of claim 12, wherein the riboswitch is inserted about 74, about 110, or about 149 nucleotides 5' of the polyadenylation signal.

16. The method of claim 12, wherein the polynucleotide construct comprises two or more riboswitches located in the 3' UTR of the target gene, wherein each riboswitch comprises an effector region and an aptamer, wherein the effector region comprises a U1 snRNP binding site and sequence complementary to the U1 snRNP binding site.

17. The method of claim 16, wherein the two or more riboswitches comprise different aptamers that specifically bind to different small molecule ligands.

18. The method of claim 16, wherein the two or more riboswitches comprise the same aptamer.

19. The method according to claim 16, wherein the two or more riboswitches are inserted at different locations of the 3' UTR of the target gene.

20. The method according to claim 12, wherein the target gene comprising the riboswitch is incorporated in a vector for the expression of the target gene.

21. The method of claim 20, wherein the vector is a viral vector.

22. The method of claim 21, wherein the viral vector is selected from the group consisting of adenoviral vector, adeno-associated virus vector, and lentiviral vector.

23. A vector comprising the polynucleotide construct of claim 1.

24. The vector of claim 23, wherein the vector is a viral vector.

25. The vector of claim 24, wherein the viral vector is selected from the group consisting of adenoviral vector, adeno-associated virus vector, and lentiviral vector.

26. The method of claim 12, wherein the effector region comprises additional sequence that is capable of forming a stem when the aptamer binds ligand.

27. The method of claim 26, wherein the effector region comprises a stem-forming sequence that is 9 to 11 base pairs.

28. The method of claim 26, wherein the effector region comprises a stem-forming sequence with one or more mismatched bases in the stem.

29. The polynucleotide construct of claim 1, wherein the riboswitch is located 87 or 140 nucleotides 5' of the polyadenylation signal.

30. The polynucleotide construct of claim 1, wherein the riboswitch is located 74, 110, or 149 nucleotides 5' of the polyadenylation signal.

* * * * *

```
                               SEQUENCE LISTING

<160> NUMBER OF SEQ ID NOS: 54

<210> SEQ ID NO 1
<211> LENGTH: 10
<212> TYPE: DNA
<213> ORGANISM: Artificial Sequence
<220> FEATURE:
<223> OTHER INFORMATION: Consensus U1 binding site

<400> SEQUENCE: 1
caggtaagta                                                              10

<210> SEQ ID NO 2
<211> LENGTH: 10
<212> TYPE: DNA
<213> ORGANISM: Artificial Sequence
<220> FEATURE:
<223> OTHER INFORMATION: Mutant U1 binding site

<400> SEQUENCE: 2
catggaacta                                                              10

<210> SEQ ID NO 3
<211> LENGTH: 210
<212> TYPE: DNA
<213> ORGANISM: Artificial Sequence
<220> FEATURE:
<223> OTHER INFORMATION: U1-87 wt in pRL-SV40

<400> SEQUENCE: 3
tcaaatcgtt cgttgagcga gttctcaaaa atgaacaata attctagagc ggccgcttcg        60
agcagacatg ataagataca ttgatgagtt tggacaaacc aggtaagtac aactagaatg       120
cagtgaaaaa aatgctttat ttgtgaaatt tgtgatgcta ttgctttatt tgtaaccatt       180
ataagctgca ataaacaagt taacaacaac                                        210

<210> SEQ ID NO 4
<211> LENGTH: 210
<212> TYPE: DNA
<213> ORGANISM: Artificial Sequence
<220> FEATURE:
<223> OTHER INFORMATION: U1-87 mut in pRL-SV40

<400> SEQUENCE: 4
tcaaatcgtt cgttgagcga gttctcaaaa atgaacaata attctagagc ggccgcttcg        60
agcagacatg ataagataca ttgatgagtt tggacaaacc atggaactac aactagaatg       120
cagtgaaaaa aatgctttat ttgtgaaatt tgtgatgcta ttgctttatt tgtaaccatt       180
ataagctgca ataaacaagt taacaacaac                                        210

<210> SEQ ID NO 5
<211> LENGTH: 212
<212> TYPE: DNA
<213> ORGANISM: Artificial Sequence
<220> FEATURE:
<223> OTHER INFORMATION: U1-140 wt in pRL-SV40

<400> SEQUENCE: 5
tcaaatcgtt cgttgagcga gttctcaaaa atgaacaata attctagaca ggtaagtagc        60
ggccgcttcg agcagacatg ataagataca ttgatgagtt tggacaaacc acaactagaa       120
```

| | |
|---|---|
| tgcagtgaaa aaaatgcttt atttgtgaaa tttgtgatgc tattgcttta tttgtaacca | 180 |
| ttataagctg caataaacaa gttaacaaca ac | 212 |

```
<210> SEQ ID NO 6
<211> LENGTH: 212
<212> TYPE: DNA
<213> ORGANISM: Artificial Sequence
<220> FEATURE:
<223> OTHER INFORMATION: U1-140 mut in pRL-SV40

<400> SEQUENCE: 6
```

| | |
|---|---|
| tcaaatcgtt cgttgagcga gttctcaaaa atgaacaata attctagaca tggaactagc | 60 |
| ggccgcttcg agcagacatg ataagataca ttgatgagtt tggacaaacc acaactagaa | 120 |
| tgcagtgaaa aaaatgcttt atttgtgaaa tttgtgatgc tattgcttta tttgtaacca | 180 |
| ttataagctg caataaacaa gttaacaaca ac | 212 |

```
<210> SEQ ID NO 7
<211> LENGTH: 228
<212> TYPE: DNA
<213> ORGANISM: Artificial Sequence
<220> FEATURE:
<223> OTHER INFORMATION: 2xU1-140 wt in pRL-SV40

<400> SEQUENCE: 7
```

| | |
|---|---|
| tcaaatcgtt cgttgagcga gttctcaaaa atgaacaata attctagaca ggtaagtaac | 60 |
| caaacaggta agtagcggcc gcttcgagca gacatgataa gatacattga tgagtttgga | 120 |
| caaaccacaa ctagaatgca gtgaaaaaaa tgctttattt gtgaaatttg tgatgctatt | 180 |
| gctttatttg taaccattat aagctgcaat aaacaagtta acaacaac | 228 |

```
<210> SEQ ID NO 8
<211> LENGTH: 228
<212> TYPE: DNA
<213> ORGANISM: Artificial Sequence
<220> FEATURE:
<223> OTHER INFORMATION: 2xU1-140 mut in pRL-SV40

<400> SEQUENCE: 8
```

| | |
|---|---|
| tcaaatcgtt cgttgagcga gttctcaaaa atgaacaata attctagaca tggaactaac | 60 |
| caaacatgga actagcggcc gcttcgagca gacatgataa gatacattga tgagtttgga | 120 |
| caaaccacaa ctagaatgca gtgaaaaaaa tgctttattt gtgaaatttg tgatgctatt | 180 |
| gctttatttg taaccattat aagctgcaat aaacaagtta acaacaac | 228 |

```
<210> SEQ ID NO 9
<211> LENGTH: 244
<212> TYPE: DNA
<213> ORGANISM: Artificial Sequence
<220> FEATURE:
<223> OTHER INFORMATION: 3xU1-140 wt in pRL-SV40

<400> SEQUENCE: 9
```

| | |
|---|---|
| tcaaatcgtt cgttgagcga gttctcaaaa atgaacaata attctagaca ggtaagtaac | 60 |
| caaacaggta agtaaccaaa caggtaagta gcggccgctt cgagcagaca tgataagata | 120 |
| cattgatgag tttggacaaa ccacaactag aatgcagtga aaaaaatgct ttatttgtga | 180 |
| aatttgtgat gctattgctt tatttgtaac cattataagc tgcaataaac aagttaacaa | 240 |
| caac | 244 |

```
<210> SEQ ID NO 10
<211> LENGTH: 244
<212> TYPE: DNA
<213> ORGANISM: Artificial Sequence
<220> FEATURE:
<223> OTHER INFORMATION: 3xU1_140 mut in pRL-SV40

<400> SEQUENCE: 10
tcaaatcgtt cgttgagcga gttctcaaaa atgaacaata attctagaca tggaactaac      60
caaacatgga actaaccaaa catggaacta gcggccgctt cgagcagaca tgataagata     120
cattgatgag tttggacaaa ccacaactag aatgcagtga aaaaaatgct ttatttgtga     180
aatttgtgat gctattgctt tatttgtaac cattataagc tgcaataaac aagttaacaa     240
caac                                                                  244

<210> SEQ ID NO 11
<211> LENGTH: 209
<212> TYPE: DNA
<213> ORGANISM: Artificial Sequence
<220> FEATURE:
<223> OTHER INFORMATION: 87-9 in pRL-SV40

<400> SEQUENCE: 11
tcaaatcgtt cgttgagcga gttctcaaaa atgaacaata attctagagc ggccgcttcg      60
agcagacatg ataagataca ttgatgagtt tggacaaacc aggtaagtca actagaatgc     120
agtgaaaaaa atgctttatt tgtgaaattt gtgatgctat tgctttattt gtaaccatta     180
taagctgcaa taaacaagtt aacaacaac                                       209

<210> SEQ ID NO 12
<211> LENGTH: 208
<212> TYPE: DNA
<213> ORGANISM: Artificial Sequence
<220> FEATURE:
<223> OTHER INFORMATION: 87-8 in pRL-SV40

<400> SEQUENCE: 12
tcaaatcgtt cgttgagcga gttctcaaaa atgaacaata attctagagc ggccgcttcg      60
agcagacatg ataagataca ttgatgagtt tggacaaacc aggtaagcaa ctagaatgca     120
gtgaaaaaaa tgctttattt gtgaaatttg tgatgctatt gctttatttg taaccattat     180
aagctgcaat aaacaagtta acaacaac                                        208

<210> SEQ ID NO 13
<211> LENGTH: 207
<212> TYPE: DNA
<213> ORGANISM: Artificial Sequence
<220> FEATURE:
<223> OTHER INFORMATION: 87-7 in pRL-SV40

<400> SEQUENCE: 13
tcaaatcgtt cgttgagcga gttctcaaaa atgaacaata attctagagc ggccgcttcg      60
agcagacatg ataagataca ttgatgagtt tggacaaacc aggtaacaac tagaatgcag     120
tgaaaaaaat gctttatttg tgaaatttgt gatgctattg ctttatttgt aaccattata     180
agctgcaata aacaagttaa caacaac                                         207

<210> SEQ ID NO 14
<211> LENGTH: 206
<212> TYPE: DNA
<213> ORGANISM: Artificial Sequence
<220> FEATURE:
```

-continued

<223> OTHER INFORMATION: 87-6 in pRL-SV40

<400> SEQUENCE: 14

| tcaaatcgtt cgttgagcga gttctcaaaa atgaacaata attctagagc ggccgcttcg | 60 |
| agcagacatg ataagataca ttgatgagtt tggacaaacc aggtacaact agaatgcagt | 120 |
| gaaaaaaatg ctttatttgt gaaatttgtg atgctattgc tttatttgta accattataa | 180 |
| gctgcaataa acaagttaac aacaac | 206 |

<210> SEQ ID NO 15
<211> LENGTH: 205
<212> TYPE: DNA
<213> ORGANISM: Artificial Sequence
<220> FEATURE:
<223> OTHER INFORMATION: 87-5 in pRL-SV40

<400> SEQUENCE: 15

| tcaaatcgtt cgttgagcga gttctcaaaa atgaacaata attctagagc ggccgcttcg | 60 |
| agcagacatg ataagataca ttgatgagtt tggacaaacc aggtcaacta gaatgcagtg | 120 |
| aaaaaaatgc tttatttgtg aaatttgtga tgctattgct ttatttgtaa ccattataag | 180 |
| ctgcaataaa caagttaaca acaac | 205 |

<210> SEQ ID NO 16
<211> LENGTH: 238
<212> TYPE: DNA
<213> ORGANISM: Artificial Sequence
<220> FEATURE:
<223> OTHER INFORMATION: U1 87-9 SL in pRL-SV40

<400> SEQUENCE: 16

| tcaaatcgtt cgttgagcga gttctcaaaa atgaacaata attctagagc ggccgcttcg | 60 |
| agcagacatg ataagataca ttgatgagtt tggacaaacc aaacccaggt aagttaccga | 120 |
| aaggtaactt acctgggcaa ctagaatgca gtgaaaaaaa tgctttattt gtgaaatttg | 180 |
| tgatgctatt gctttatttg taaccattat aagctgcaat aaacaagtta acaacaac | 238 |

<210> SEQ ID NO 17
<211> LENGTH: 238
<212> TYPE: DNA
<213> ORGANISM: Artificial Sequence
<220> FEATURE:
<223> OTHER INFORMATION: U1 87-9 SL broken in pRL-SV40

<400> SEQUENCE: 17

| tcaaatcgtt cgttgagcga gttctcaaaa atgaacaata attctagagc ggccgcttcg | 60 |
| agcagacatg ataagataca ttgatgagtt tggacaaacc aaacccaggt aagttaccga | 120 |
| aaaaacaaa caaaaaacaa ctagaatgca gtgaaaaaaa tgctttattt gtgaaatttg | 180 |
| tgatgctatt gctttatttg taaccattat aagctgcaat aaacaagtta acaacaac | 238 |

<210> SEQ ID NO 18
<211> LENGTH: 267
<212> TYPE: DNA
<213> ORGANISM: Artificial Sequence
<220> FEATURE:
<223> OTHER INFORMATION: U1_theo_1 in pRL-SV40

<400> SEQUENCE: 18

| tcaaatcgtt cgttgagcga gttctcaaaa atgaacaata attctagagc ggccgcttcg | 60 |
| agcagacatg ataagataca ttgatgagtt tggacaaacc aaacccaggt aagttaccgg | 120 |

```
cgataccagc cgaaaggccc ttggcagcgt cggtaactta cctgggcaac tagaatgcag    180
tgaaaaaaat gctttatttg tgaaatttgt gatgctattg ctttatttgt aaccattata    240
agctgcaata aacaagttaa caacaac                                        267
```

<210> SEQ ID NO 19
<211> LENGTH: 265
<212> TYPE: DNA
<213> ORGANISM: Artificial Sequence
<220> FEATURE:
<223> OTHER INFORMATION: U1_theo_2 in pRL-SV40

<400> SEQUENCE: 19

```
tcaaatcgtt cgttgagcga gttctcaaaa atgaacaata attctagagc ggccgcttcg     60
agcagacatg ataagataca ttgatgagtt tggacaaacc aaacccaggt aagttacggc    120
gataccagcc gaaaggccct tggcagcgtc gtaacttacc tgggcaacta gaatgcagtg    180
aaaaaaatgc tttatttgtg aaatttgtga tgctattgct ttatttgtaa ccattataag    240
ctgcaataaa caagttaaca acaac                                          265
```

<210> SEQ ID NO 20
<211> LENGTH: 263
<212> TYPE: DNA
<213> ORGANISM: Artificial Sequence
<220> FEATURE:
<223> OTHER INFORMATION: U1_theo_3 in pRL-SV40

<400> SEQUENCE: 20

```
tcaaatcgtt cgttgagcga gttctcaaaa atgaacaata attctagagc ggccgcttcg     60
agcagacatg ataagataca ttgatgagtt tggacaaacc aaacccaggt aagttacgcg    120
ataccagccg aaaggcccstt ggcagcgtgt aacttacctg gcaactaga atgcagtgaa    180 aaaaatgctt tatttgtgaa atttgtgatg ctattgcttt atttgtaacc attataagct    240
gcaataaaca agttaacaac aac                                            263
```

<210> SEQ ID NO 21
<211> LENGTH: 261
<212> TYPE: DNA
<213> ORGANISM: Artificial Sequence
<220> FEATURE:
<223> OTHER INFORMATION: U1_theo_4 in pRL-SV40

<400> SEQUENCE: 21

```
tcaaatcgtt cgttgagcga gttctcaaaa atgaacaata attctagagc ggccgcttcg     60
agcagacatg ataagataca ttgatgagtt tggacaaacc aaacccaggt aagttagcga    120
taccagccga aaggcccttg gcagcgttaa cttacctggg caactagaat gcagtgaaaa    180
aaatgcttta tttgtgaaat ttgtgatgct attgctttat ttgtaaccat tataagctgc    240
aataaacaag ttaacaacaa c                                              261
```

<210> SEQ ID NO 22
<211> LENGTH: 259
<212> TYPE: DNA
<213> ORGANISM: Artificial Sequence
<220> FEATURE:
<223> OTHER INFORMATION: U1_theo_5 in pRL-SV40

<400> SEQUENCE: 22

```
tcaaatcgtt cgttgagcga gttctcaaaa atgaacaata attctagagc ggccgcttcg      60
agcagacatg ataagataca ttgatgagtt tggacaaacc aaacccaggt aagttacgat     120
accagccgaa aggcccttgg cagcgtaact tacctgggca actagaatgc agtgaaaaaa     180
atgctttatt tgtgaaattt gtgatgctat tgctttattt gtaaccatta taagctgcaa     240
taaacaagtt aacaacaac                                                  259
```

<210> SEQ ID NO 23
<211> LENGTH: 257
<212> TYPE: DNA
<213> ORGANISM: Artificial Sequence
<220> FEATURE:
<223> OTHER INFORMATION: U1_theo_6 in pRL-SV40

<400> SEQUENCE: 23

```
tcaaatcgtt cgttgagcga gttctcaaaa atgaacaata attctagagc ggccgcttcg      60
agcagacatg ataagataca ttgatgagtt tggacaaacc aaacccaggt aagttcgata     120
ccagccgaaa ggcccttggc agcgaactta cctgggcaac tagaatgcag tgaaaaaaat     180
gctttatttg tgaaatttgt gatgctattg ctttatttgt aaccattata agctgcaata     240
aacaagttaa caacaac                                                    257
```

<210> SEQ ID NO 24
<211> LENGTH: 255
<212> TYPE: DNA
<213> ORGANISM: Artificial Sequence
<220> FEATURE:
<223> OTHER INFORMATION: U1_theo_7 in pRL-SV40

<400> SEQUENCE: 24

```
tcaaatcgtt cgttgagcga gttctcaaaa atgaacaata attctagagc ggccgcttcg      60
agcagacatg ataagataca ttgatgagtt tggacaaacc aaacccaggt aagttgatac     120
cagccgaaag gcccttggca gcaacttacc tgggcaacta gaatgcagtg aaaaaaatgc     180
tttatttgtg aaatttgtga tgctattgct ttatttgtaa ccattataag ctgcaataaa     240
caagttaaca acaac                                                      255
```

<210> SEQ ID NO 25
<211> LENGTH: 253
<212> TYPE: DNA
<213> ORGANISM: Artificial Sequence
<220> FEATURE:
<223> OTHER INFORMATION: U1_theo_8 in pRL-SV40

<400> SEQUENCE: 25

```
tcaaatcgtt cgttgagcga gttctcaaaa atgaacaata attctagagc ggccgcttcg      60
agcagacatg ataagataca ttgatgagtt tggacaaacc aaacccaggt aagtgatacc     120
agccgaaagg cccttggcag cacttacctg gcaactaga atgcagtgaa aaaatgctt      180 tatttgtgaa atttgtgatg ctattgcttt atttgtaacc attataagct gcaataaaca     240
agttaacaac aac                                                        253
```

<210> SEQ ID NO 26
<211> LENGTH: 251
<212> TYPE: DNA
<213> ORGANISM: Artificial Sequence
<220> FEATURE:

<223> OTHER INFORMATION: U1_theo_9 in pRL-SV40

<400> SEQUENCE: 26

| | | |
|---|---|---|
| tcaaatcgtt cgttgagcga gttctcaaaa atgaacaata attctagagc ggccgcttcg | 60 |
| agcagacatg ataagataca ttgatgagtt tggacaaacc aaacccaggt aagtatacca | 120 |
| gccgaaaggc ccttggcaga cttacctggg caactagaat gcagtgaaaa aaatgcttta | 180 |
| tttgtgaaat ttgtgatgct attgctttat ttgtaaccat tataagctgc aataaacaag | 240 |
| ttaacaacaa c | 251 |

<210> SEQ ID NO 27
<211> LENGTH: 253
<212> TYPE: DNA
<213> ORGANISM: Artificial Sequence
<220> FEATURE:
<223> OTHER INFORMATION: U1_theo_8_1 in pRL-SV40

<400> SEQUENCE: 27

| | | |
|---|---|---|
| tcaaatcgtt cgttgagcga gttctcaaaa atgaacaata attctagagc ggccgcttcg | 60 |
| agcagacatg ataagataca ttgatgagtt tggacaaacc aaacccaggt aagtgatacc | 120 |
| agccgaaagg cccttggcag cacttacctg gacaactaga atgcagtgaa aaaatgctt | 180 |
| tatttgtgaa atttgtgatg ctattgcttt atttgtaacc attataagct gcaataaaca | 240 |
| agttaacaac aac | 253 |

<210> SEQ ID NO 28
<211> LENGTH: 253
<212> TYPE: DNA
<213> ORGANISM: Artificial Sequence
<220> FEATURE:
<223> OTHER INFORMATION: U1_theo_8_2 in pRL-SV40

<400> SEQUENCE: 28

| | | |
|---|---|---|
| tcaaatcgtt cgttgagcga gttctcaaaa atgaacaata attctagagc ggccgcttcg | 60 |
| agcagacatg ataagataca ttgatgagtt tggacaaacc aaacccaggt aagtgatacc | 120 |
| agccgaaagg cccttggcag cacttacctg aacaactaga atgcagtgaa aaaatgctt | 180 |
| tatttgtgaa atttgtgatg ctattgcttt atttgtaacc attataagct gcaataaaca | 240 |
| agttaacaac aac | 253 |

<210> SEQ ID NO 29
<211> LENGTH: 253
<212> TYPE: DNA
<213> ORGANISM: Artificial Sequence
<220> FEATURE:
<223> OTHER INFORMATION: U1_theo_8_3 in pRL-SV40

<400> SEQUENCE: 29

| | | |
|---|---|---|
| tcaaatcgtt cgttgagcga gttctcaaaa atgaacaata attctagagc ggccgcttcg | 60 |
| agcagacatg ataagataca ttgatgagtt tggacaaacc aaacccaggt aagtgatacc | 120 |
| agccgaaagg cccttggcag cacttaccta acaactaga atgcagtgaa aaaatgctt | 180 |
| tatttgtgaa atttgtgatg ctattgcttt atttgtaacc attataagct gcaataaaca | 240 |
| agttaacaac aac | 253 |

<210> SEQ ID NO 30
<211> LENGTH: 253
<212> TYPE: DNA
<213> ORGANISM: Artificial Sequence

```
<220> FEATURE:
<223> OTHER INFORMATION: U1_theo_8_4 in pRL-SV40

<400> SEQUENCE: 30
tcaaatcgtt cgttgagcga gttctcaaaa atgaacaata attctagagc ggccgcttcg      60
agcagacatg ataagataca ttgatgagtt tggacaaacc aaacccaggt aagtgatacc     120
agccgaaagg cccttggcag cacttaccaa aacaactaga atgcagtgaa aaaaatgctt    180
tatttgtgaa atttgtgatg ctattgcttt atttgtaacc attataagct gcaataaaca    240
agttaacaac aac                                                        253

<210> SEQ ID NO 31
<211> LENGTH: 253
<212> TYPE: DNA
<213> ORGANISM: Artificial Sequence
<220> FEATURE:
<223> OTHER INFORMATION: U1_theo_8_5 in pRL-SV40

<400> SEQUENCE: 31
tcaaatcgtt cgttgagcga gttctcaaaa atgaacaata attctagagc ggccgcttcg      60
agcagacatg ataagataca ttgatgagtt tggacaaacc aaacccaggt aagtgatacc     120
agccgaaagg cccttggcag cacttacaaa aacaactaga atgcagtgaa aaaaatgctt    180
tatttgtgaa atttgtgatg ctattgcttt atttgtaacc attataagct gcaataaaca    240
agttaacaac aac                                                        253

<210> SEQ ID NO 32
<211> LENGTH: 253
<212> TYPE: DNA
<213> ORGANISM: Artificial Sequence
<220> FEATURE:
<223> OTHER INFORMATION: U1_theo_8_6 in pRL-SV40

<400> SEQUENCE: 32
tcaaatcgtt cgttgagcga gttctcaaaa atgaacaata attctagagc ggccgcttcg      60
agcagacatg ataagataca ttgatgagtt tggacaaacc aaacccaggt aagtgatacc     120
agccgaaagg cccttggcag cacttaaaaa aacaactaga atgcagtgaa aaaaatgctt    180
tatttgtgaa atttgtgatg ctattgcttt atttgtaacc attataagct gcaataaaca    240
agttaacaac aac                                                        253

<210> SEQ ID NO 33
<211> LENGTH: 253
<212> TYPE: DNA
<213> ORGANISM: Artificial Sequence
<220> FEATURE:
<223> OTHER INFORMATION: U1_theo_8_7 in pRL-SV40

<400> SEQUENCE: 33
tcaaatcgtt cgttgagcga gttctcaaaa atgaacaata attctagagc ggccgcttcg      60
agcagacatg ataagataca ttgatgagtt tggacaaacc aaacccaggt aagtgatacc     120
agccgaaagg cccttggcag cacttcaaaa aacaactaga atgcagtgaa aaaaatgctt    180
tatttgtgaa atttgtgatg ctattgcttt atttgtaacc attataagct gcaataaaca    240
agttaacaac aac                                                        253

<210> SEQ ID NO 34
<211> LENGTH: 253
<212> TYPE: DNA
```

<213> ORGANISM: Artificial Sequence
<220> FEATURE:
<223> OTHER INFORMATION: U1_theo_8_8 in pRL-SV40

<400> SEQUENCE: 34

```
tcaaatcgtt cgttgagcga gttctcaaaa atgaacaata attctagagc ggccgcttcg    60
agcagacatg ataagataca ttgatgagtt tggacaaacc aaacccaggt aagtgatacc   120
agccgaaagg cccttggcag cactacaaaa acaactaga atgcagtgaa aaaaatgctt   180
tatttgtgaa atttgtgatg ctattgcttt atttgtaacc attataagct gcaataaaca   240
agttaacaac aac                                                      253
```

<210> SEQ ID NO 35
<211> LENGTH: 253
<212> TYPE: DNA
<213> ORGANISM: Artificial Sequence
<220> FEATURE:
<223> OTHER INFORMATION: U1_theo_8_9 in pRL-SV40

<400> SEQUENCE: 35

```
tcaaatcgtt cgttgagcga gttctcaaaa atgaacaata attctagagc ggccgcttcg    60
agcagacatg ataagataca ttgatgagtt tggacaaacc aaacccaggt aagtgatacc   120
agccgaaagg cccttggcag cacaacaaaa acaactaga atgcagtgaa aaaaatgctt   180
tatttgtgaa atttgtgatg ctattgcttt atttgtaacc attataagct gcaataaaca   240
agttaacaac aac                                                      253
```

<210> SEQ ID NO 36
<211> LENGTH: 251
<212> TYPE: DNA
<213> ORGANISM: Artificial Sequence
<220> FEATURE:
<223> OTHER INFORMATION: U1_theo_9_1 in pRL-SV40

<400> SEQUENCE: 36

```
tcaaatcgtt cgttgagcga gttctcaaaa atgaacaata attctagagc ggccgcttcg    60
agcagacatg ataagataca ttgatgagtt tggacaaacc aaacccaggt aagtatacca   120
gccgaaaggc ccttggcaga cttacctgga caactagaat gcagtgaaaa aaatgcttta   180
tttgtgaaat tgtgatgct attgctttat tgtaaccat tataagctgc aataaacaag   240
ttaacaacaa c                                                        251
```

<210> SEQ ID NO 37
<211> LENGTH: 251
<212> TYPE: DNA
<213> ORGANISM: Artificial Sequence
<220> FEATURE:
<223> OTHER INFORMATION: U1_theo_9_2 in pRL-SV40

<400> SEQUENCE: 37

```
tcaaatcgtt cgttgagcga gttctcaaaa atgaacaata attctagagc ggccgcttcg    60
agcagacatg ataagataca ttgatgagtt tggacaaacc aaacccaggt aagtatacca   120
gccgaaaggc ccttggcaga cttacctgaa caactagaat gcagtgaaaa aaatgcttta   180
tttgtgaaat tgtgatgct attgctttat tgtaaccat tataagctgc aataaacaag   240
ttaacaacaa c                                                        251
```

<210> SEQ ID NO 38
<211> LENGTH: 251

```
<212> TYPE: DNA
<213> ORGANISM: Artificial Sequence
<220> FEATURE:
<223> OTHER INFORMATION: U1_theo_9_3 in pRL-SV40

<400> SEQUENCE: 38
tcaaatcgtt cgttgagcga gttctcaaaa atgaacaata attctagagc ggccgcttcg    60
agcagacatg ataagataca ttgatgagtt tggacaaacc aaacccaggt aagtatacca   120
gccgaaaggc ccttggcaga cttacctaaa caactagaat gcagtgaaaa aaatgctttta  180 tttgtgaaat ttgtgatgct attgctttat ttgtaaccat tataagctgc aataaacaag   240
ttaacaacaa c                                                         251

<210> SEQ ID NO 39
<211> LENGTH: 251
<212> TYPE: DNA
<213> ORGANISM: Artificial Sequence
<220> FEATURE:
<223> OTHER INFORMATION: U1_theo_9_4 in pRL-SV40

<400> SEQUENCE: 39
tcaaatcgtt cgttgagcga gttctcaaaa atgaacaata attctagagc ggccgcttcg    60
agcagacatg ataagataca ttgatgagtt tggacaaacc aaacccaggt aagtatacca   120
gccgaaaggc ccttggcaga cttaccaaaa caactagaat gcagtgaaaa aaatgctttta  180 tttgtgaaat ttgtgatgct attgctttat ttgtaaccat tataagctgc aataaacaag   240
ttaacaacaa c                                                         251

<210> SEQ ID NO 40
<211> LENGTH: 251
<212> TYPE: DNA
<213> ORGANISM: Artificial Sequence
<220> FEATURE:
<223> OTHER INFORMATION: U1_theo_9_5 in pRL-SV40

<400> SEQUENCE: 40
tcaaatcgtt cgttgagcga gttctcaaaa atgaacaata attctagagc ggccgcttcg    60
agcagacatg ataagataca ttgatgagtt tggacaaacc aaacccaggt aagtatacca   120
gccgaaaggc ccttggcaga cttacaaaaa caactagaat gcagtgaaaa aaatgctttta  180 tttgtgaaat ttgtgatgct attgctttat ttgtaaccat tataagctgc aataaacaag   240
ttaacaacaa c                                                         251

<210> SEQ ID NO 41
<211> LENGTH: 251
<212> TYPE: DNA
<213> ORGANISM: Artificial Sequence
<220> FEATURE:
<223> OTHER INFORMATION: U1_theo_9_6 in pRL-SV40

<400> SEQUENCE: 41
tcaaatcgtt cgttgagcga gttctcaaaa atgaacaata attctagagc ggccgcttcg    60
agcagacatg ataagataca ttgatgagtt tggacaaacc aaacccaggt aagtatacca   120
gccgaaaggc ccttggcaga cttaaaaaaa caactagaat gcagtgaaaa aaatgctttta  180 tttgtgaaat ttgtgatgct attgctttat ttgtaaccat tataagctgc aataaacaag   240
ttaacaacaa c                                                         251

<210> SEQ ID NO 42
```

```
<211> LENGTH: 251
<212> TYPE: DNA
<213> ORGANISM: Artificial Sequence
<220> FEATURE:
<223> OTHER INFORMATION: U1_theo_9_7 in pRL-SV40

<400> SEQUENCE: 42
tcaaatcgtt cgttgagcga gttctcaaaa atgaacaata attctagagc ggccgcttcg      60
agcagacatg ataagataca ttgatgagtt tggacaaacc aaacccaggt aagtatacca     120
gccgaaaggc ccttggcaga cttcaaaaaa caactagaat gcagtgaaaa aaatgcttta     180
tttgtgaaat ttgtgatgct attgctttat ttgtaaccat tataagctgc aataaacaag     240
ttaacaacaa c                                                         251

<210> SEQ ID NO 43
<211> LENGTH: 251
<212> TYPE: DNA
<213> ORGANISM: Artificial Sequence
<220> FEATURE:
<223> OTHER INFORMATION: U1_theo_9_8 in pRL-SV40

<400> SEQUENCE: 43
tcaaatcgtt cgttgagcga gttctcaaaa atgaacaata attctagagc ggccgcttcg      60
agcagacatg ataagataca ttgatgagtt tggacaaacc aaacccaggt aagtatacca     120
gccgaaaggc ccttggcaga ctacaaaaaa caactagaat gcagtgaaaa aaatgcttta     180
tttgtgaaat ttgtgatgct attgctttat ttgtaaccat tataagctgc aataaacaag     240
ttaacaacaa c                                                         251

<210> SEQ ID NO 44
<211> LENGTH: 539
<212> TYPE: DNA
<213> ORGANISM: Artificial Sequence
<220> FEATURE:
<223> OTHER INFORMATION: 4xU1_theo_8_1 in pRL-SV40

<400> SEQUENCE: 44
tcaaatcgtt cgttgagcga gttctcaaaa atgaacaata attctagagc ggccgcttcg      60
agcagacatg ataagataca ttgatgagtt tggacaaacc aaacccaggt aagtgatacc     120
agccgaaagg cccttggcag cacttacctg acaactaga atgcagtgaa aaaagagttt     180
ggacaaacca aacccaggta agtgatacca gccgaaaggc ccttggcagc acttacctgg     240
acaactagaa tgcagtgaaa aaatgcgag tttggacaaa ccaaacccag gtaagtgata     300
ccagccgaaa ggcccttggc agcacttacc tggacaacta gaatgcagtg aaaaaaatgc     360
tttatttgtg agagtttgga caaaccaaac ccaggtaagt gataccagcc gaaaggccct     420
tggcagcact tacctggaca actagaatgc agtgaaaaaa atgctttatt tgtgaaattt     480
gtgatgctat tgctttattt gtaaccatta taagctgcaa taaacaagtt aacaacaac     539

<210> SEQ ID NO 45
<211> LENGTH: 328
<212> TYPE: DNA
<213> ORGANISM: Artificial Sequence
<220> FEATURE:
<223> OTHER INFORMATION: U1_Gua_1 wt in pFLuc

<400> SEQUENCE: 45
tcataaaggc caagaagggc ggaaagatcg ccgtgtaagc cataccacat taaggtaatg      60
tataatcgcg tggatatggc acgcaagttt ctaccgggca ccgtaaatgt ccgactacat     120
```

-continued

```
tactgtagag gttttacttg ctttaaaaaa cctcccacac ctcccctga acctgaaaca    180 taaaatgaat gcaattgttg ttgttaactt gtttattgca gcttataatg gttacaaata    240
aagcaatagc atcacaaatt tcacaaataa agcatttttt tcactgcatt ctagttgtgg    300
tttgtccaaa ctcatcaatg tatcttaa                                       328
```

<210> SEQ ID NO 46
<211> LENGTH: 328
<212> TYPE: DNA
<213> ORGANISM: Artificial Sequence
<220> FEATURE:
<223> OTHER INFORMATION: U1_Gua_1 mut in pFLuc

<400> SEQUENCE: 46

```
tcataaaggc caagaagggc ggaaagatcg ccgtgtaagc cataccacat taatggaatc    60
tataatcgcg tggatatggc acgcaagttt ctaccgggca ccgtaaatgt ccgactagat    120
tcctgtagag gttttacttg ctttaaaaaa cctcccacac ctcccctga acctgaaaca     180 taaaatgaat gcaattgttg ttgttaactt gtttattgca gcttataatg gttacaaata    240
aagcaatagc atcacaaatt tcacaaataa agcatttttt tcactgcatt ctagttgtgg    300
tttgtccaaa ctcatcaatg tatcttaa                                       328
```

<210> SEQ ID NO 47
<211> LENGTH: 328
<212> TYPE: DNA
<213> ORGANISM: Artificial Sequence
<220> FEATURE:
<223> OTHER INFORMATION: U1_Gua_2 wt in pFLuc

<400> SEQUENCE: 47

```
tcataaaggc caagaagggc ggaaagatcg ccgtgtaagc cataccacat ttgtagaggt    60
tttacttgct ttaaaaaacc tcccacacct aaggtaatgt ataatcgcgt ggatatggca    120
cgcaagtttc taccgggcac cgtaaatgtc cgactacatt accccctga acctgaaaca     180 taaaatgaat gcaattgttg ttgttaactt gtttattgca gcttataatg gttacaaata    240
aagcaatagc atcacaaatt tcacaaataa agcatttttt tcactgcatt ctagttgtgg    300
tttgtccaaa ctcatcaatg tatcttaa                                       328
```

<210> SEQ ID NO 48
<211> LENGTH: 328
<212> TYPE: DNA
<213> ORGANISM: Artificial Sequence
<220> FEATURE:
<223> OTHER INFORMATION: U1_Gua_2 mut in pFLuc

<400> SEQUENCE: 48

```
tcataaaggc caagaagggc ggaaagatcg ccgtgtaagc cataccacat ttgtagaggt    60
tttacttgct ttaaaaaacc tcccacacct aatggaatct ataatcgcgt ggatatggca    120
cgcaagtttc taccgggcac cgtaaatgtc cgactagatt ccccccctga acctgaaaca    180
taaaatgaat gcaattgttg ttgttaactt gtttattgca gcttataatg gttacaaata    240
aagcaatagc atcacaaatt tcacaaataa agcatttttt tcactgcatt ctagttgtgg    300
tttgtccaaa ctcatcaatg tatcttaa                                       328
```

<210> SEQ ID NO 49
<211> LENGTH: 328
<212> TYPE: DNA

<213> ORGANISM: Artificial Sequence
<220> FEATURE:
<223> OTHER INFORMATION: U1_Gua_3 wt in pFLuc

<400> SEQUENCE: 49

| | | |
|---|---|---|
| tcataaaggc caagaagggc ggaaagatcg ccgtgtaagc cataccacat ttgtagaggt | 60 |
| tttacttgct ttaaaaaacc tcccacacct cccCctgaac ctgaaacata aaatgaatgc | 120 |
| aattgtaagg taatgtataa tcgcgtggat atggcacgca agtttctacc gggcaccgta | 180 |
| aatgtccgac tacattactg ttgttaactt gtttattgca gcttataatg gttacaaata | 240 |
| aagcaatagc atcacaaatt tcacaaataa agcattttt tcactgcatt ctagttgtgg | 300 |
| tttgtccaaa ctcatcaatg tatcttaa | 328 |

<210> SEQ ID NO 50
<211> LENGTH: 328
<212> TYPE: DNA
<213> ORGANISM: Artificial Sequence
<220> FEATURE:
<223> OTHER INFORMATION: U1_Gua_3 mut in pFLuc

<400> SEQUENCE: 50

| | | |
|---|---|---|
| tcataaaggc caagaagggc ggaaagatcg ccgtgtaagc cataccacat ttgtagaggt | 60 |
| tttacttgct ttaaaaaacc tcccacacct cccCctgaac ctgaaacata aaatgaatgc | 120 |
| aattgtaatg gaatctataa tcgcgtggat atggcacgca agtttctacc gggcaccgta | 180 |
| aatgtccgac tagattcctg ttgttaactt gtttattgca gcttataatg gttacaaata | 240 |
| aagcaatagc atcacaaatt tcacaaataa agcattttt tcactgcatt ctagttgtgg | 300 |
| tttgtccaaa ctcatcaatg tatcttaa | 328 |

<210> SEQ ID NO 51
<211> LENGTH: 375
<212> TYPE: DNA
<213> ORGANISM: Artificial Sequence
<220> FEATURE:
<223> OTHER INFORMATION: wtU1_Gua_HBGPA

<400> SEQUENCE: 51

| | | |
|---|---|---|
| tcataaaggc caagaagggc ggaaagatcg ccgtgtaagg atccaagctt atcgataccg | 60 |
| tcgacctcga ggtaatgtat aatcgcgtgg atatggcacg caagtttcta ccgggcaccg | 120 |
| taaatgtccg actacattac ggcccagatc taattcaccc caccagtgca ggctgcctat | 180 |
| cagaaagtgg tggctggtgt ggctaatgcc ctggcccaca agtatcacta agctcgcttt | 240 |
| cttgctgtcc aatttctatt aaaggttcct ttgttcccta agtccaacta ctaaactggg | 300 |
| ggatattatg aagggccttg agcatctgga ttctgcctaa taaaaaacat ttattttcat | 360 |
| tgcaatgatg tattt | 375 |

<210> SEQ ID NO 52
<211> LENGTH: 375
<212> TYPE: DNA
<213> ORGANISM: Artificial Sequence
<220> FEATURE:
<223> OTHER INFORMATION: mutU1_Gua_HBGPA

<400> SEQUENCE: 52

| | | |
|---|---|---|
| tcataaaggc caagaagggc ggaaagatcg ccgtgtaagg atccaagctt atcgataccg | 60 |
| tcgacctcga tggaatctat aatcgcgtgg atatggcacg caagtttcta ccgggcaccg | 120 |
| taaatgtccg actacattac ggcccagatc taattcaccc caccagtgca ggctgcctat | 180 |

-continued

```
cagaaagtgg tggctggtgt ggctaatgcc ctggcccaca agtatcacta agctcgcttt      240
cttgctgtcc aatttctatt aaaggttcct ttgttcccta agtccaacta ctaaactggg      300
ggatattatg aagggccttg agcatctgga ttctgcctaa taaaaaacat ttattttcat      360
tgcaatgatg tattt                                                      375

<210> SEQ ID NO 53
<211> LENGTH: 8
<212> TYPE: DNA
<213> ORGANISM: Artificial Sequence
<220> FEATURE:
<223> OTHER INFORMATION: U1 binding site

<400> SEQUENCE: 53 caggtaag                                                                8

<210> SEQ ID NO 54
<211> LENGTH: 9
<212> TYPE: DNA
<213> ORGANISM: Artificial Sequence
<220> FEATURE:
<223> OTHER INFORMATION: U1 binding site

<400> SEQUENCE: 54 caggtaagt                                                               9
```